US008771942B2

(12) United States Patent
Belvin et al.

(10) Patent No.: US 8,771,942 B2
(45) Date of Patent: Jul. 8, 2014

(54) SCDS AS MODIFIERS OF THE P53 PATHWAY AND METHODS OF USE

(75) Inventors: Marcia Belvin, Albany, CA (US); Helen Francis-Lang, San Francisco, CA (US); Lori Friedman, San Carlos, CA (US); Gregory D. Plowman, San Carlos, CA (US); Timothy S. Heuer, Pacifica, CA (US)

(73) Assignee: Exelixis, Inc., South San Francisco, CA (US)

( * ) Notice: Subject to any disclaimer, the term of this patent is extended or adjusted under 35 U.S.C. 154(b) by 322 days.

(21) Appl. No.: 12/714,257

(22) Filed: Feb. 26, 2010

(65) Prior Publication Data
US 2010/0159470 A1 Jun. 24, 2010

Related U.S. Application Data

(63) Continuation of application No. 11/852,890, filed on Sep. 10, 2007, now abandoned, which is a continuation of application No. 10/377,133, filed on Feb. 28, 2003, now abandoned.

(60) Provisional application No. 60/361,196, filed on Mar. 1, 2002.

(51) Int. Cl.
*C12Q 1/68* (2006.01)
(52) U.S. Cl.
USPC .......................................... 435/6.1
(58) Field of Classification Search
None
See application file for complete search history.

(56) References Cited

U.S. PATENT DOCUMENTS 7,132,529 B2 * 11/2006 Crooke et al. ............... 536/24.5

FOREIGN PATENT DOCUMENTS

| WO | 00/09754 | | 2/2000 |
| WO | WO 01/62954 | * | 2/2001 |
| WO | 01/53468 | | 7/2001 |
| WO | 01/66757 | | 9/2001 |
| WO | 02/26944 | | 4/2002 |
| WO | 02/46465 | | 6/2002 |

OTHER PUBLICATIONS

Zamore (Nature Structural Biology, 2001, vol. 8, No. 9, pp. 746-750).*
Li, Juan et al., "Partial Characterization of a cDNA for Human Stearoly-CoA Desaturase and Changes in its MRNA Expression in Some Normal and Malignant Tissues", Int. J. Cnacer: 57, 348-352 (1994).
Li, J. et al., "Homo sapiens stearoly-CoA desaturase (delta-9-desaturase) (SCD), mRNA", Genbank GI No. 19923295, 2002.
Hoshino, T. et al., "Homo sapiens Scd m RNA for stearoly-CoA desaturase, complete cds", Genbank GI No. 7415720, 2000.
Zhang, C. et al., "Homo sapiens PRO0998 mRNA, complete cds", Genbank GI No. 7959734, 2001.
Strausberg, R., "Homo sapiens, clone MGC:10270 Image:3959199, mRNA, complete cds", Genbank GI No. 13623379, 2001.
Strausberg, R., "Homo sapiens, clone MGC:10264 Image:3844850, mRNA, complete cds", Genbank GI No. 13543283, 2001.
Zhang, L. et al., "Homo sapiens stearoly-CoA desaturase (SCD) mRNA, complete cds", Genbank GI No. 4808600, 1999.
Logan, T. J. et al., "Sequence 1 from Patent WO0166758", Genbank GI No. 15859548, 2001.
Strausberg, R., "Homo sapiens, clone MGC:10777 Image:3607979, mRNA, complete cds", Genbank GI No. 13436280, 2001.
Sugano, S. et al., "Homo sapiens hypothetical protein FLJ21032 (FLJ21032), mRNA", Genbank GI No. 13376362.
Li. J. et al., "Stearoly-CoA desaturase (delta-9-desaturase) [Homo sapiens]", Genbank GI No. 4826990. 2001.
Li, J. et al., "Stearoly-CoA desaturase (delta-9-desaturase) [Homo sapiens]", Genbank GI No. 19923296, 2002.
Logan, T. J. et al., "Unnamed protein product [Homo sapiens]", Genbank GI No. 15859549, 2001.
Bork, Genome Research, vol. 10, 398-400, 2000.
Smith et al., Nature Biotechnology, vol. 15, 1222-1223, 1997.
Brenner, TIG, vol. 15, 132-133, 1999.
Broun et al., Science, vol. 282, 1315-1317, 1998.
Van De Loo et al., Proc. Natl. Acad. Sci., vol. 92, 6743-6747, 1995.

* cited by examiner

*Primary Examiner* — Celine Qian
(74) *Attorney, Agent, or Firm* — McDonnell Boehnen Hulbert & Berghoff LLP

(57) ABSTRACT

Human SCD genes are identified as modulators of the p53 pathway, and thus are therapeutic targets for disorders associated with defective p53 function. Methods for identifying modulators of p53, comprising screening for agents that modulate the activity of SCD are provided.

6 Claims, No Drawings

SEQUENCE LISTING

<160> NUMBER OF SEQ ID NOS: 30

<210> SEQ ID NO 1
<211> LENGTH: 5221

<212> TYPE: DNA
<213> ORGANISM: Homo sapiens

<400> SEQUENCE: 1

| | | | | | |
|---|---|---|---|---|---|
| ataaaagggg | gctgaggaaa | taccggacac | ggtcacccgt | tgccagctct | agcctttaaa | 60 |
| ttcccggctc | ggggacctcc | acgcaccgcg | gctagcgccg | acaaccagct | agcgtgcaag | 120 |
| gcgccgcggc | tcagcgcgta | ccggcgggct | tcgaaaccgc | agtcctccgg | cgaccccgaa | 180 |
| ctccgctccg | gagcctcagc | ccctggaaa | gtgatcccgg | catccgagag | ccaagatgcc | 240 |
| ggcccacttg | ctgcaggacg | atatctctag | ctcctatacc | accaccacca | ccattacagc | 300 |
| gcctccctcc | agggtcctgc | agaatggagg | agataagttg | gagacgatgc | ccctctactt | 360 |
| ggaagacgac | attcgccctg | atataaaaga | tgatatatat | gaccccacct | acaaggataa | 420 |
| ggaaggccca | agccccaagg | ttgaatatgt | ctggagaaac | atcatcctta | tgtctctgct | 480 |
| acacttggga | gccctgtatg | ggatcacttt | gattcctacc | tgcaagttct | acacctggct | 540 |
| ttgggggta | ttctactatt | ttgtcagtgc | cctgggcata | acagcaggag | ctcatcgtct | 600 |
| gtggagccac | cgctcttaca | aagctcggct | gccctacgg | ctctttctga | tcattgccaa | 660 |
| cacaatggca | ttccagaatg | atgtctatga | atgggctcgt | gaccaccgtg | cccaccacaa | 720 |
| gttttcagaa | acacatgctg | atcctcataa | ttcccgacgt | ggcttttct | tctctcacgt | 780 |
| gggttggctg | cttgtgcgca | aacacccagc | tgtcaaagag | aaggggagta | cgctagactt | 840 |
| gtctgaccta | gaagctgaga | aactggtgat | gttccagagg | aggtactaca | aacctggctt | 900 |
| gctgctgatg | tgcttcatcc | tgcccacgct | tgtgccctgg | tatttctggg | gtgaaacttt | 960 |
| tcaaaacagt | gtgttcgttg | ccactttctt | gcgatatgct | gtggtgctta | atgccacctg | 1020 |
| gctggtgaac | agtgctgccc | acctcttcgg | atatcgtcct | tatgacaaga | acattagccc | 1080 |
| ccgggagaat | atcctggttt | cacttggagc | tgtgggtgag | ggcttccaca | actaccacca | 1140 |
| ctcctttccc | tatgactact | ctgccagtga | gtaccgctgg | cacatcaact | tcaccacatt | 1200 |
| cttcattgat | tgcatggccg | ccctcggtct | ggcctatgac | cggaagaaag | tctccaaggc | 1260 |
| cgccatcttg | gccaggatta | aaagaaccgg | agatggaaac | tacaagagtg | gctgagtttg | 1320 |
| gggtccctca | ggtttccttt | ttcaaaaacc | agccaggcag | aggttttaat | gtctgtttat | 1380 |
| taactactga | ataatgctac | caggatgcta | aagatgatga | tgttaaccca | ttccagtaca | 1440 |
| gtattctttt | aaaattcaaa | agtattgaaa | gccaacaact | ctgcctttat | gatgctaagc | 1500 |
| tgatattatt | tcttctctta | tcctctctct | cttctaggcc | cattgtcctc | cttttcactt | 1560 |
| tattgctatc | gccctccttt | cccttattgc | ctcccaggca | agcagctggt | cagtctttgc | 1620 |
| tcagtgtcca | gcttccaaag | cctagacaac | cttctctgtag | cctaaaacga | atggtctttg | 1680 |
| ctccagataa | ctctctttcc | ttgagctgtt | gtgagctttg | aagtaggtgg | cttgagctag | 1740 |
| agataaaaca | gaatcttctg | ggtagtcccc | tgttgattat | cttcagccca | ggcttttgct | 1800 |
| agatggaatg | gaaaagcaac | ttcatttgac | acaaagcttc | taaagcaggt | aaattgtcgg | 1860 |
| gggagagagt | tagcatgtat | gaatgtaagg | atgagggaag | cgaagcaaga | ggaacctctc | 1920 |
| gccatgatca | gacatacagc | tgcctaccta | atgaggactt | caagcccac | cacatagcat | 1980 |
| gcttcctttc | tctcctggct | cggggtaaaa | agtggctgcg | gtgtttggca | atgctaattc | 2040 |
| aatgccgcaa | catatagttg | aggccgagga | taaagaaaag | acattttaag | tttgtagtaa | 2100 |
| aagtggtctc | tgctggggaa | gggttttctt | ttcttttttt | ctttaataac | aaggagattt | 2160 |
| cttagttcat | atatcaagaa | gtcttgaagt | tgggtgtttc | cagaattggt | aaaaacagca | 2220 |

-continued

```
gctcatggaa ttttgagtat tccatgagct gctcattaca gttctttcct ctttctgctc    2280
tgccatcttc aggatattgg ttcttcccct catagtaata agatggctgt ggcatttcca    2340
aacatccaaa aaagggaag gatttaagga ggtgaagtcg ggtcaaaaat aaaatatata    2400
tacatatata cattgcttag aacgttaaac tattagagta tttcccttcc aaagagggat    2460
gtttggaaaa aactctgaag gagaggagga attagttggg atgccaattt cctctccact    2520
gctggacatg agatggagag gctgagggac aggatctata ggcagcttct aagagcgaac    2580
ttcacatagg aagggatctg agaacacgtt gccagggct tgagaaggtt actgagtgag    2640
ttattgggag tcttaataaa ataaactaga tattaggtcc attcattaat tagttccagt    2700
ttctccttga aatgagtaaa aactagaagg cttctctcca cagtgttgtg cccttcact    2760 catttttttt tgaggagaag ggggtctctg ttaacatcta gcctaaagta tacaactgcc    2820 tgggggggcag ggttaggaat ctcttcacta ccctgattct tgattcctgg ctctaccctg    2880
tctgtccctt ttcttttgacc agatctttct cttccctgaa cgttttcttc tttccctgga    2940
caggcagcct cctttgtgtg tattcagagg cagtgatgac ttgctgtcca ggcagctccc    3000
tcctgcacac agaatgctca gggtcactga accactgctt ctcttttgaa agtagagcta    3060
gctgccactt tcacgtggcc tccgcagtgt ctccacctac accctgtgc tcccctgcca    3120 cactgatggc tcaagacaag gctggcaaac cctcccagaa acatctctgg cccagaaagc    3180
ctctctctcc ctcctctct catgaggcac agccaagcca agcgctcatg ttgagccagt    3240
gggccagcca cagagcaaaa gagggtttat tttcagtccc ctctctctgg gtcagaacca    3300
gagggcatgc tgaatgcccc ctgcttactt ggtgagggtg ccccgcctga gtcagtgctc    3360
tcagctggca gtgcaatgct tgtagaagta ggaggaaaca gttctcactg ggaagaagca    3420
agggcaagaa cccaagtgcc tcacctcgaa aggaggccct gttccctgga gtcagggtga    3480
actgcaaagc tttggctgag acctgggatt tgagatacca caaaccctgc tgaacacagt    3540
gtctgttcag caaactaacc agcattccct acagcctagg gcagacaata gtatagaagt    3600
ctggaaaaaa acaaaaacag aatttgagaa ccttggacca ctcctgtccc tgtagctcag    3660
tcatcaaagc agaagtctgg ctttgctcta ttaagattgg aaatgtacac taccaaacac    3720
tcagtccact gttgagcccc agtgctggaa gggaggaagg ccttcttct gtgttaattg    3780 cgtagaggct acaggggtta gcctggacta aaggcatcct tgtctttga gctattcacc    3840 tcagtagaaa aggatctaag ggaagatcac tgtagtttag ttctgttgac ctgtgcacct    3900
accccttgga aatgtctgct ggtatttcta attccacagg tcatcagatg cctgcttgat    3960
aatatataaa caataaaaac aactttcact tcttcctatt gtaatcgtgt gccatggatc    4020
tgatctgtac catgaccta cataaggctg gatggcacct caggctgagg gccccaatgt    4080
atgtgtggct gtgggtgtgg gtgggagtgt gtctgctgag taaggaacac gattttcaag    4140
attctaaagc tcaattcaag tgacacatta atgataaact cagatctgat caagagtccg    4200
gatttctaac agtccctgct ttgggggtg tgctgacaac ttagctcagg tgccttacat    4260
cttttctaat cacagtgttg catatgagcc tgccctcact ccctctgcag aatcccttg    4320 cacctgagac cctactgaag tggctggtag aaaaagggc ctgagtggag gattatcagt    4380
atcacgattt gcaggattcc cttctgggct tcattctgga aacttttgtt agggctgctt    4440
ttcttaagtg cccacatttg atggagggtg gaaataattt gaatgtattt gatttataag    4500
tttttttttt ttttgggtt aaaagatggt tgtagcattt aaaatggaaa attttctcct    4560
tggtttgcta gtatcttggg tgtattctct gtaagtgtag ctcaaatagg tcatcatgaa    4620
```

```
aggttaaaaa agcgaggtgg ccatgttatg ctggtggtta aggccagggc ctctccaacc    4680
actgtgccac tgacttgctg tgtgaccctg ggcaagtcac ttaactataa ggtgcctcag    4740
ttttccttct gttaaaatgg ggataataat actgacctac ctcaaagggc agttttgagg    4800
catgactaat gctttttaga aagcattttg ggatccttca gcacaggaat tctcaagacc    4860
tgagtatttt ttataatagg aatgtccacc atgaacttga tacgtccgtg tgtcccagat    4920
gctgtcatta gtctatatgg ttctccaaga aactgaatga atccattgga gaagcggtgg    4980
ataactagcc agacaaaatt tgagaataca taaacaacgc attgccacgg aaacatacag    5040
aggatgcctt ttctgtgatt gggtgggatt ttttcccttt ttatgtggga tatagtagtt    5100
acttgtgaca aaaataattt tggaataatt tctattaata tcaactctga agctaattgt    5160
actaatctga gattgtgttt gttcataata aaagtgaagt gaatctaaaa aaaaaaaaa    5220 a                                                                    5221

<210> SEQ ID NO 2
<211> LENGTH: 5329
<212> TYPE: DNA
<213> ORGANISM: Homo sapiens
<220> FEATURE:
<221> NAME/KEY: misc_feature
<222> LOCATION: (1986)..(1986)
<223> OTHER INFORMATION: n is a, c, g, or t

<400> SEQUENCE: 2
gtggtgtcgg tgtcggcagc atccccggcg ccctgctgcg gtcgccggag ccctcggcct     60
ctgttctcct ccccctcccg cccttacctc cacgcgggac cgcccgcgcc agtcaactcc    120
tcgcactttg cccctgcttg gcagcggata aaggggggct gaggaaatac cggacacgtc    180
cacccgttgc cagctctagc ctttaaattc ccggctcggg acctcacgc accgggctag    240 cgccgacaac cagctagcgt gcaaggcgcc gcggctcagc gcgtaccggc gggcttcgaa    300
accgcagtcc tccggcgacc ccgaactccg ctccggagcc tcagcccct ggaaagtgat    360 cccggcatcg gagagccaag atgccggccc acttgctgca ggacgatatc tctagctcct    420
ataccaccac caccaccatt acagcgcctc cctccagggt cctgcagaat ggaggagata    480
agttggagac gatgcccctc tacttggaag acgacattcg ccctgatata aagatgata    540 tatatgaccc cacctacaag gataaggaag gcccaagccc caaggttgaa tatgtctgga    600
gaaacatcat ccttatgtct ctgctacact gggagccct gtatgggatc actttgattc    660
ctacctgcaa gttctacacc tggctttggg gggtattcta ctattttgtc agtgccctgg    720
gcataacagc aggagctcat cgtctgtgga gccaccgctc ttacaaagct cggctgcccc    780
tacggctctt tctgatcatt gccaacacaa tggcattcca gaatgatgtc tatgaatggg    840
ctcgtgacca ccgtgcccac cacaagtttt cagaaacaca tgctgatcct cataattccc    900
gacgtggctt tttcttctct cacgtgggtt ggctgcttgt gcgcaaacac ccagctgtca    960
aagagaaggg gagtacgcta gacttgtctg acctagaagc tgagaaactg gtgatgttcc    1020
agaggaggta ctacaaacct ggcttgctgc tgatgtgctt catcctgccc acgcttgtgc    1080
cctggtattt ctggggtgaa acttttcaaa acagtgtgtt cgttgccact tcttgcgat    1140 atgctgtggt gcttaatgcc acctggctgg tgaacagtgc tgcccacctc ttcggatatc    1200
gtccttatga caagaacatt agcccccggg agaatatcct ggtttcactt ggagctgtgg    1260
gtgagggctt ccacaactac caccactcct ttccctatga ctactctgcc agtgagtacc    1320
```

```
gctggcacat caacttcacc acattcttca ttgattgcat ggccgccctc ggtctggcct    1380
atgaccggaa gaaagtctcc aaggccgcca tcttggccag gattaaaaga accggagatg    1440
gaaactacaa gagtggctga gtttgggggtc cctcaggttc cttttttcaaa aaccagccag    1500 gcagaggttt taatgtctgt ttattaacta ctgaataatg ctaccaggat gctaaagatg    1560
atgatgttaa cccattccag tacagtattc ttttaaaatt caaaagtatt gaaagccaac    1620
aactctgcct ttatgatgct aagctgatat tatttcttct cttatcctct ctctcttcta    1680
ggcccattgt cctcctttc actttaatcg ccctcctttc ccttattgcc tcccaggcaa    1740
gcagctggtc agtctttgct cagtgtccag cttccaaagc ctagacaacc tttctgtagc    1800
ctaaaacgaa tggtctttgc tccagataac tctctttcct tgagctgttg tgagctttga    1860
agtaggtggc ttgagctaga gataaaacag aatcttctgg gtagtcccct gttgattatc    1920
ttcagcccag gcttttgcta gatggaatgg aaaagcaact tcatttgaca caaagcttct    1980
aaagcnaggt aaattgtcgg gggagagagt tagcatgtat gaatgtaagg atgagggaag    2040
cgaaggaacc tctcgccatg atcagacata cagctgccta cctaatgagg acttcaagcc    2100
ccaccacata gcatgcttcc tttctctcct ggctcggggt aaaaagtggc tgcggtgttt    2160
ggcaatgcta attcaatgcc gcaacatata gttgaggccg aggataaaga aaagacattt    2220
taagtttgta gtaaaagtgg tctctgctgg ggaagggttt tcttttcttt ttttctttaa    2280
taacaaggag atttcttagt tcatatatca agaagtcttg aagttgggtg tttccagaat    2340
tggtaaaaac agcagctcat agaattttga gtattccatg agctgctcat tacagttctt    2400
tcctctttct gctctgccat cttcaggata ttggttcttc ccctcatagt aataagatgg    2460
ctgtggcatt tccaaacatc caaaaaaagg gaaggattta aggaggtgaa gtcgggtcaa    2520
aaataaaata tatatacata tatacattgc ttagaacgtt aaactattag agtatttccc    2580
ttccaaagag ggatgtttgg aaaaaactct gaaggagagg aggaattagt tgggatgcca    2640
atttcctctc cactgctgga catgagatgg agaggctgag ggacaggatc tataggcagc    2700
ttctaagagc gaacttcaca taggaaggga tctgagaaca cgttcagggg ttgagaaggt    2760
tactgagtga gttattggga gtcttaataa actagatatt aggtccattc attaattagt    2820
tccagtttct ccttgaaatg agtaaaaact agaaggcttc tctccacagt gttgtgcccc    2880
ttcactcatt ttttttttgag gagaagggggg tctctgttaa catctagcct aaagtataca    2940
aactgcctgg ggggcagggt taggaatctc ttcactaccc tgattcttga ttcctggctc    3000
taccctgtct gtccctttc tttgaccaga tctttctctt ccctgaacgt tttcttcttt    3060
ccctggacag gcagcctcct tgtgtgtat tcagaggcag tgatgacttg ctgtccaggc    3120
agctccctcc tgcacacaga atgctcaggg tcactgaacc actgcttctc ttttgaaagt    3180
agagctagct gccactttca cgtggcctcc gcagtgtctc cacctacacc cctgtgctcc    3240
cctgccacac tgatggctca agacaaggct ggcaaaccct cccagaaaca tctctggccc    3300
agaaagcctc tctctcccctc cctctctcat gagaagccaa gcgctcatgt tgagccagtg    3360
ggccagccac agagcaaaag agggtttatt ttcagtcccc tctctctggg tcagaaccag    3420
agggcatgct gaatgccccc tgcttacttg gtgagggtgc cccgcctgag tcagtgctct    3480
cagctggcag tgcaatgctt gtagaagtag gaggaaacag ttctcactgg gaagaagcaa    3540
gggcaagaac ccaagtgcct cacctcgaaa ggaggccctg ttccctggag tcagggtgaa    3600
ctgcaaagct ttggctgaga cctgggattt gagataccac aaaccctgct gaacacagtg    3660
tctgttcagc aaactaacca gcattcccta cagcctaggg cagacaatag tatagaagtc    3720
```

```
tggaaaaaaa caaaaacaga atttgagaac cttggaccac tcctgtccct gtagctcagt    3780
catcaaagca gaagtctggc tttgctctat taagattgga aatgtacact accaaacact    3840
cagtccactg ttgagcccca gtgctggaag ggaggaaggc ctttcttctg tgttaattgc    3900
gtagaggcta caggggttag cctggactaa aggcatcctt gtctttgagc tattcacctc    3960
agtagaaaag gatctaaggg aagatcactg tagtttagtt ctgttgacct gtgcacctac    4020
cccttggaaa tgtctgctgg tatttctaat tccacaggtc atcagatgcc tgcttgataa    4080
tatataaaca ataaaaacaa cttttcacttc ttcctattgt aatcgtgtgc catggatctg    4140
atctgtacca tgaccctaca taaggctgga tggcacctca ggctgagggc cccaatgtat    4200
gtgtggctgt gggtgtgggt gggagtgtgt ctgctgagta aggaacacga ttttcaagat    4260
tctaaagctc aattcaagtg acacattaat gataaactca gatctgatca agagtccgga    4320
tttctaacag tccttgcttt ggggggtgtg ctggcaactt agctcaggtg ccttacatct    4380
tttctaatca cagtgttgca tatgagcctg ccctcactcc ctctgcagaa tcccttgca    4440 cctgagaccc tactgaagtg gctggtagaa aaaggggcct gagtggagga ttatcagtat    4500
cacgatttgc aggattccct tctgggcttc attctggaaa cttttgttag ggctgctttt    4560
cttaagtgcc cacatttgat ggagggtgga ataatttgaa atgtatttga tttataagtt    4620
tttttttttt tttgggttaa aagatggttg tagcatttaaa aatggaaaaat tttctccttg    4680 gtttgctagt atcttgggtg tattctctgt aagtgtagct caaataggtc atcatgaaag    4740
gttaaaaaag cgaggtggcc atgttatgct ggtggttgcc agggcctcca accactgtgc    4800
cactgacttg ctgtgtgacc ctgggcaagt cacttaacta aaggtgcct cagttttcct    4860 tctgttaaaa tggggataat aatactgacc tacctcaaag ggcagttttg aggcatgact    4920
aatgcttttt agaaagcatt tgggatcct tcagcacagg aattctcaag acctgagtat    4980 ttttttataat aggaatgtcc accatgaact tgatacgtcc gtgtgtccca gatgctgtca    5040
ttagtctata tggttctcca agaaactgaa tgaatccatt ggagaagcgg tggataacta    5100
gccagacaaa atttgagaat acataaacaa cgcattgcca cggaaacata cagaggatgc    5160
cttttctgtg attgggtggg attttttccc tttttatgtg ggatatagta gttacttgtg    5220
acaagaataa ttttggaata atttctatta atatcaactc tgaagctaat tgtactaatc    5280
tgagattgtg tttgttcata ataaaagtga agtgaatctg attgcactg                5329
```

<210> SEQ ID NO 3
<211> LENGTH: 1649
<212> TYPE: DNA
<213> ORGANISM: Homo sapiens
<400> SEQUENCE: 3

```
ctgcttgcct gggaggcaat aagggaaagg agggcgatag caataaagtg aaaaggagga      60
caatgggcct agaagagaga gaggataaga gaagaaataa tatcagctta gcatcataaa    120
ggcagagttg ttggctttca atactttga attttaaaag aatactgtac tggaatgggt     180
taacatcatc atctttagca tcctggtagc attattcagt agttaataaa cagacattaa    240
aacctctgcc tggctggttt ttgaaaaagg aacctgaggg accccaaact cagccactct    300
tgtagtttcc atctccggtt cttttaatcc tggccaagat ggcggccttg gagactttct    360
tccggtcata ggccagaccg agggcggcca tgcaatcaat gaagaatgtg gtgaagttga    420
tgtgccagcg gtactcactg gcagagtagt cataggaaa ggagtggtgg tagttgtgga    480
```

-continued

```
agccctcacc cacagctcca agtgaaacca ggatattctc ccgggggcta atgttcttgt    540
cataaggacg atatccgaag aggtgggcag cactgttcac cagccaggtg cattaagca     600
ccacagcata tcgcaagaaa gtggcaacga acacactgtt ttgaaaagtt tcaccccaga    660
aataccaggg cacaagcgtg gcaggatga agcacatcat cagcaagcca ggtttgtagt     720
acctcctctg gaacatcacc agtttctcag cttctaggtc agacaagtct agcgtactcc    780
ccttctcttt gacagctggg tgtttgcgca caagcagcca acccacgtga gagaagaaaa    840
agccacgtcg ggaattatga ggatcagcat gtgtttctga aaacttgtgg tgggcacggt    900
ggtcacgagc ccattcatag acatcattct ggaatgccat tgtgttggca atgatcagaa    960
agagccgtag gggcagccga gctttgtaag agcggtggct ccacagacga tgagctcctg   1020
ctgttatgcc cagggcactg acaaaatagt agaatacccc ccaaagccag gtgtagaact   1080
tgcaggtagg aatcaaagtg atcccataca gggctcccaa gtgtagcaga gacataagga   1140
tgatgtttct ccagacatat caaccttgg ggcttgggcc ttccttatcc ttgtaggtgg    1200
ggtcatatat atcatctttt atatcagggc gaatgtcgtc ttccaagtag aggggcatcg   1260
tctccaactt atctcctcca ttctgcagga ccctggaggg aggcgctgta atggtggtgg   1320
tggtggtata ggagcttttg tagagaagtg ctgcaaggct gacgataagg agacctgctt   1380
tgccgaggag ggtaaaaaac ttgttgctgc aagtcaagct gccttaggct tataacatca   1440
catttaaaag catctcagcc taccatgaga ataagagaaa gaaatgaag atcaaaagct    1500
tattcatctg ttttctttt tcgttggtgt aaagccaaca ccctgtctaa aaacataaa    1560
tttctttaat cattttgcct cttttctctg tgcttcaatt aataaaaat ggaaagaatc   1620
taaaaaaaaa aaaaaaaaa aaaaaaaaa                                      1649
```

<210> SEQ ID NO 4
<211> LENGTH: 1064
<212> TYPE: DNA
<213> ORGANISM: Homo sapiens

<400> SEQUENCE: 4

```
ggcacgaggg agagtctgtt tttcttccta aaatttggac tcttgtctgc acaaacactg     60
ggcataacag caggagcgct ggaacattct gcctcttgag tgaaggggcc ttcttttctag   120
cctctatggc actgaggggt gcgccggctg gtggaggagt agtccgatgg agccctgcgt    180
tccccgggga cacagggcca agctttgagg tggaaagttt ctggttctga aacaaagctc    240
ggctgcccct acggctcttt ctgatcattg ccaacacaat ggcattccag aatgatgtct    300
atgaatgggc tcgtgaccac cgtgcccacc acaagttttc agaaacacat gctgatcctc    360
ataattcccg acgtggcttt ttcttctctc acgtgggttg gctgcttgtg cgcaaacacc    420
cagctgtcaa agagaagggg agtacgctag acttgtctga cctagaagct gagaaactgg    480
tgatgttcca gaggaggtac tacaaacctg gcttgctgat gatgtgcttc atcctgccca    540
cgcttgtgcc ctggtatttc tggggtgaaa ctttttcaaaa cagtgtgttc gttgccactt    600
tcttgcgata tgctgtggtg cttaatgcca cctggctggt gaacagtgct gcccacctct    660
tcggatatcg tccttatgac aagaacatta gccccgggga gaatatcctg gtttcacttg    720
agctgtgggg tgagggcttc cacaactacc accactcctt tccctatgac tactctgcca    780
gtgagtaccg ctggcacatc aacttcacca cattcttcat tgattgcatg gccgccctcg    840
gtctggccta tgaccggaag aaagtctcca aggccgccac cttggccagg attaaaagaa    900
ccggagatgg aaactacaag agtggctgag tttggggtcc ctcaggttcc ttttttcaaaa   960
```

| | | |
|---|---|---|
| accagccagg cagaggtttt aatgtctgtt tattaactac tgaataatgc taccaggatg | 1020 |
| ctaaagatga tgatgttaac ccattccaaa aaaaaaaaaa aaaa | 1064 |

<210> SEQ ID NO 5
<211> LENGTH: 1323
<212> TYPE: DNA
<213> ORGANISM: Homo sapiens

<400> SEQUENCE: 5

| | |
|---|---|
| ggcacgagga attcccggct cggggacctc cacgcaccgc ggctagcgcc gacaaccagc | 60 |
| tagcgtgcaa ggcgccgcgg ctcagcgcgt accggcgggc ttcgaaaccg cagtcctccg | 120 |
| gcgaccccga actccgctcc ggagcctcag cccctggaa agtgatcccg gcatccgaga | 180 |
| gccaagatgc cggcccactt gctgcaggac gatatctcta gctcctatac caccaccacc | 240 |
| accattacag cgcctccctc agggtcctg cagaatggag gagataagtt ggagacgatg | 300 |
| cccctctact tggaagacga cattcgcccct gatataaaag atgatatata tgaccccacc | 360 |
| tacaaggata aggaaggccc aagccccaag gttgaatatg tctggagaaa catcatcctt | 420 |
| atgtctctgc tacacttggg agccctgtat gggatcactt tgattcctac ctgcaagttc | 480 |
| tacacctggc tttgggggt attctactat tttgtcagtg ccctgggcat aacagcagga | 540 |
| gctcatcgtc tgtggagcca ccgctcttac aaagctcggc tgcccctacg gctctttctg | 600 |
| atcattgcca acacaatggc attccagaat gatgtctatg aatgggctcg tgaccaccgt | 660 |
| gcccaccaca gtttttcaga acacatgct gatcctcata ttcccgacg tggcttttc | 720 |
| ttctctcacg tgggttggct gcttgtgcgc aaacacccag ctgtcaaaga aaggggagt | 780 |
| acgctagact tgtctgacct agaagctgag aaactggtga tgttccagag gaggtactac | 840 |
| aaacctggct tgctgatgat gtgcttcatc ctgcccacgc ttgtgccctg gtatttctgg | 900 |
| ggtgaaactt ttcaaaacag tgtgttcgtt gccactttct tgcgatatgc tgtggtgctt | 960 |
| aatgccacct ggctggtgaa cagtgctgcc caccttttcg gatatcgtcc ttatgacaag | 1020 |
| aacattagcc cccgggagaa tatcctggtt tcacttggag ctgtgggtga gggcttccac | 1080 |
| aactaccacc actcctttcc ctatgactac tctgccagtg agtaccgctg gcacatcaac | 1140 |
| ttcaccacat tcttcattga ttgcatggcc gccctcggtc tggcctatga ccggaagaaa | 1200 |
| gtctccaagg ccgccatctt ggccaggatt aaaagaaccg agatggaaa ctaaaaaaaa | 1260 |
| aaaaaaaaaa aaaaaaaaaa aaaaaaaaaa aaaaaaaaaa aaaataaaaa aaaaaaaaaa | 1320 |
| aaa | 1323 |

<210> SEQ ID NO 6
<211> LENGTH: 5221
<212> TYPE: DNA
<213> ORGANISM: Homo sapiens

<400> SEQUENCE: 6

| | |
|---|---|
| ataaaagggg gctgaggaaa taccggacac ggtcacccgt tgccagctct agcctttaaa | 60 |
| ttcccggctc ggggacctcc acgcaccgcg gctagcgccg acaaccagct agcgtgcaag | 120 |
| gcgccgcggc tcagcgcgta ccggcgggct tcgaaaccg cagtcctccgg cgaccccgaa | 180 |
| ctccgctccg gagcctcagc cccctggaaa gtgatcccgg catccgagag ccaagatgcc | 240 |
| ggcccacttg ctgcaggacg atatctctag ctcctatacc accaccacca ccattacagc | 300 |
| gcctccctcc agggtcctgc agaatggagg agataagttg gagacgatgc ccctctactt | 360 |

```
ggaagacgac attcgccctg atataaaaga tgatatatat gaccccacct acaaggataa    420
ggaaggccca agccccaagg ttgaatatgt ctggagaaac atcatcctta tgtctctgct    480
acacttggga gccctgtatg ggatcacttt gattcctacc tgcaagttct acacctggct    540 ttgggggta ttctactatt ttgtcagtgc cctgggcata acagcaggag ctcatcgtct     600
gtggagccac cgctcttaca aagctcggct gcccctacgg ctctttctga tcattgccaa    660
cacaatggca ttccagaatg atgtctatga atgggctcgt gaccaccgtg cccaccacaa    720
gttttcagaa acacatgctg atcctcataa ttcccgacgt ggcttttttct tctctcacgt   780 gggttggctg cttgtgcgca aacacccagc tgtcaaagag aaggggagta cgctagactt    840
gtctgaccta gaagctgaga aactggtgat gttccagagg aggtactaca aacctggctt    900
gctgctgatg tgcttcatcc tgcccacgct tgtgccctgg tatttctggg gtgaaacttt    960
tcaaaacagt gtgttcgttg ccactttctt gcgatatgct gtggtgctta atgccacctg    1020
gctggtgaac agtgctgccc acctcttcgg atatcgtcct tatgacaaga acattagccc    1080
ccgggagaat atcctggttt cacttggagc tgtgggtgag ggcttccaca actaccacca    1140 ctccttttccc tatgactact ctgccagtga gtaccgctgg cacatcaact tcaccacatt    1200
cttcattgat tgcatggccg ccctcggtct ggcctatgac cggaagaaag tctccaaggc    1260
cgccatcttg gccaggatta aaagaaccgg agatggaaac tacaagagtg gctgagtttg    1320
gggtccctca ggtttccttt ttcaaaaacc agccaggcag aggttttaat gtctgttat    1380 taactactga ataatgctac caggatgcta aagatgatga tgttaaccca ttccagtaca    1440
gtattctttt aaaattcaaa agtattgaaa gccaacaact ctgcctttat gatgctaagc    1500
tgatattatt tcttctctta tcctctctct cttctaggcc cattgtcctc cttttcactt    1560
tattgctatc gccctccttt cccttattgc ctcccaggca agcagctggt cagtctttgc    1620
tcagtgtcca gcttccaaag cctagacaac cttctgtag cctaaaacga atggtctttg     1680
ctccagataa ctctctttcc ttgagctgtt gtgagctttg aagtaggtgg cttgagctag    1740
agataaaaca gaatcttctg ggtagtcccc tgttgattat cttcagccca ggcttttgct    1800
agatggaatg gaaaagcaac ttcatttgac acaaagcttc taaagcaggt aaattgtcgg    1860
gggagagagt tagcatgtat gaatgtaagg atgagggaag cgaagcaaga ggaacctctc    1920
gccatgatca gacatacagc tgcctaccta atgaggactt caagcccac cacatagcat     1980 gcttcctttc tctcctggct cggggtaaaa agtggctgcg gtgtttggca atgctaattc    2040
aatgccgcaa catatagttg aggccgagga taaagaaaag acattttaag tttgtagtaa    2100
aagtggtctc tgctggggaa gggttttctt ttctttttt ctttaataac aaggagattt      2160
cttagttcat atatcaagaa gtcttgaagt tgggtgtttc cagaattggt aaaaacagca    2220
gctcatggaa ttttgagtat tccatgagct gctcattaca gttctttcct ctttctgctc    2280
tgccatcttc aggatattgg ttcttcccct catagtaata agatggctgt ggcatttcca    2340
aacatccaaa aaagggaag gatttaagga ggtgaagtcg ggtcaaaaat aaaatatata     2400
tacatatata cattgcttag aacgttaaac tattagagta tttcccttcc aaagagggat    2460
gtttggaaaa aactctgaag gagaggagga attagttggg atgccaattt cctctccact    2520
gctggacatg agatggagag gctgagggac aggatctata ggcagcttct aagagcgaac    2580
ttcacatagg aagggatctg agaacacgtt gccaggggct tgagaaggtt actgagtgag    2640
ttattgggag tcttaataaa ataaactaga tattaggtcc attcattaat tagttccagt    2700
ttctccttga aatgagtaaa aactagaagg cttctctcca cagtgttgtg cccttcact     2760
```

```
catttttttt tgaggagaag ggggtctctg ttaacatcta gcctaaagta tacaactgcc   2820 tgggggggcag ggttaggaat ctcttcacta ccctgattct tgattcctgg ctctaccctg   2880
tctgtcccTt ttctttgacc agatctttct cttccctgaa cgttttcttc tttccctgga   2940
caggcagcct cctttgtgtg tattcagagg cagtgatgac ttgctgtcca ggcagctccc   3000
tcctgcacac agaatgctca gggtcactga accactgctt ctcttttgaa agtagagcta   3060
gctgccactt tcacgtggcc tccgcagtgt ctccacctac accccgtgc tccctgcca   3120 cactgatggc tcaagacaag gctggcaaac cctcccagaa acatctctgg cccagaaagc   3180
ctctctctcc ctccctctct catgaggcac agccaagcca agcgctcatg ttgagccagt   3240
gggccagcca cagagcaaaa gagggtttat tttcagtccc ctctctctgg gtcagaacca   3300
gagggcatgt tgaatgcccc ctgcttactt ggtgagggtg ccccgcctga gtcagtgctc   3360
tcagctggca gtgcaatgct tgtagaagta ggaggaaaca gttctcactg ggaagaagca   3420
agggcaagaa cccaagtgcc tcacctcgaa aggaggccct gttccctgga gtcagggtga   3480
actgcaaagc tttggctgag acctgggatt tgagatacca caaaccctgc tgaacacagt   3540
gtctgttcag caaactaacc agcattccct acagcctagg gcagacaata gtatagaagt   3600
ctggaaaaaa acaaaaacag aatttgagaa ccttggacca ctcctgtccc tgtagctcag   3660
tcatcaaagc agaagtctgg cttTgctcta ttaagattgg aaatgtacac taccaaacac   3720
tcagtccact gttgagcccc agtgctgaa gggaggaagg cctttcttct gtgttaattg   3780
cgtagaggct acaggggtta gcctggacta aaggcatcct tgtcttttga gctattcacc   3840
tcagtagaaa aggatctaag ggaagatcac tgtagtttag ttctgttgac ctgtgcacct   3900 acccccttgga aatgtctgct ggtatttcta attccacagg tcatcagatg cctgcttgat   3960
aatatataaa caataaaaac aacttTcact tcttcctatt gtaatcgtgt gccatggatc   4020
tgatctgtac catgacccta cataaggctg gatggcacct caggctgagg gccccaatgt   4080
atgtgtggct gtgggtgtgg gtgggagtgt gtctgctgag taaggaacac gattttcaag   4140
attctaaagc tcaattcaag tgacacatta atgataaact cagatctgat caagagtccg   4200
gatttctaac agtccctgct ttgggggtg tgctgacaac ttagctcagg tgccttacat   4260
cttttctaat cacagtgttg catatgagcc tgccctcact ccctctgcag aatcccttTg   4320
cacctgagac cctactgaag tggctggtag aaaaagggc ctgagtggag gattatcagt   4380
atcacgattt gcaggattcc cttctgggct tcattctgga aacttttgtt agggctgctt   4440
ttcttaagtg cccacatttg atggagggtg gaaataattt gaatgtattt gatttataag   4500 ttttttttt ttttgggtt aaaagatggt tgtagcattt aaaatggaaa attttctcct   4560
tggtttgcta gtatcttggg tgtattctct gtaagtgtag ctcaaatagg tcatcatgaa   4620
aggttaaaaa agcgaggtgg ccatgttatg ctggtggtta aggccagggc ctctccaacc   4680
actgtgccac tgacttgctg tgtgaccctg ggcaagtcac ttaactataa ggtgcctcag   4740
ttttccttct gttaaaatgg ggataataat actgacctac ctcaaagggc agttttgagg   4800
catgactaat gctttttaga aagcattttg ggatccttca gcacaggaat tctcaagacc   4860
tgagtatttt ttataatagg aatgtccacc atgaacttga tacgtccgtg tgtcccagat   4920
gctgtcatta gtctatatgg ttctccaaga aactgaatga atccattgga gaagcggtgg   4980
ataactagcc agcaaaaatt tgagaataca taaacaacgc attgcacgg aaacatacag   5040 aggatgcctt ttctgtgatt gggtgggatt ttttcccttt ttatgtggga tatagtagtt   5100
```

```
acttgtgaca aaataatttt tggaataatt tctattaata tcaactctga agctaattgt    5160
actaatctga gattgtgttt gttcataata aaagtgaagt gaatctaaaa aaaaaaaaa    5220 a                                                                   5221

<210> SEQ ID NO 7
<211> LENGTH: 1512
<212> TYPE: DNA
<213> ORGANISM: Homo sapiens

<400> SEQUENCE: 7
ccacgcgtcc ggactagttc catttccaca gctcctcctc cccggccgcg cgcccctccc     60
gccccgcgcg cgcctcctct ttctcgcggc cgagttcagc ccgggcagcc atatggggga    120
tacgccagca acagacgccg gccgccaaga tctgcatccc taggccacgc taagaccctg    180
gggaagagcg caggagcccg ggagaagggc tggaaggagg ggactggacg tgcggagaat    240 tccccctaa aaggcagaag cccccgcccc caccctcgag ctccgctcgg gcagagcgcc     300
tgcctgcctg ccgctgctgc gggcgcccac ctcgcccagc catgccaggc ccggccaccg    360
acgcggggaa gatccctttc tgcgacgcca aggaagaaat ccgtgccggg ctcgaaagct    420
ctgagggcgg cggcggcccg gagaggccag gcgcgcgcgg gcagcggcag aacatcgtct    480
ggaggaatgt cgtcctgatg agcttgctcc acttgggggc cgtgtactcc ctggtgctca    540
tccccaaagc caagccactc actctgctct gggcctactt ctgcttcctc ctggccgctc    600
tgggtgtgac agctggtgcc catcgcttgt ggagccacag gtcctaccgg gccaagctgc    660
ctctgaggat atttctggct gtcgccaact ccatggcttt ccagaatgac atcttcgagt    720
ggtccaggga ccaccgagcc caccacaagt actcagagac ggatgctgac ccccacaatg    780
cccgccgggg cttcttcttc tcccatattg ggtggctgtt gttcgcaag catcgagatg    840 ttattgagaa ggggagaaag cttgacgtca ctgacctgct tgctgatcct gtggtccgga    900
tccagagaaa gtactataag atctccgtgg tgctcatgtg cttgtggtc cccacgctgg     960 tgccctggta catctgggga gagagtctgt ggaattccta cttcttggcc tctattctcc    1020
gctataccat ctcactcaac atcagctggc tggtcaacag cgccgcccac atgtatggaa    1080
accggcccta tgacaagcac atcagccctc ggcagaaccc actcgtcgct ctgggtgcca    1140
ttggtgaagg cttccataat taccatcaca ccttttccctt tgactactct gcgagtgaat    1200
ttggcttaaa ttttaaccca accacctggt tcattgattt catgtgctgg ctggggctgg    1260
ccactgaccg caaacgggca accaagccga tgatcgaggc ccggaaggcc aggactggag    1320
acagcagtgc ttgaacttgg aacagccatc ccacatgtct gccgttgcaa cctcggttca    1380
tggctttggt tacaatagct ctcttgtaca ttggatcgtg ggaggggggca gagggtgggg    1440 aaggaacgag tcaatgtggt ttgggaatgt ttttgtttat ctcaaaataa tgttgaaata    1500
caattatcaa tg                                                       1512

<210> SEQ ID NO 8
<211> LENGTH: 865
<212> TYPE: DNA
<213> ORGANISM: Homo sapiens

<400> SEQUENCE: 8
cgccagcaac agacgccggc cgccaagatc tgcatcccta ggccacgcta agaccctggg     60
gaagagcgca ggagcccggg agaagggctg gaaggagggg actggacgtg cggagaattc    120 cccctaaaa ggcagaagcc cccgccccca ccctcgagct ccgctcgggc agagcgcctg     180
```

```
cctgcctgcc gctgctgcgg gcgcccacct cgcccagcca tgccaggccc ggccaccgac      240
gcggggaaga tcccttcctg cgacgccaag gaagaaatcc gtgccgggct cgaaagctct      300
gagggcggcg gcggcccgga gaggccaggc gcgcgcgggc agcggcagaa catcgtctgg      360
aggaatgtcg tcctgatgag cttgctccac ttggggccg tgtactccct ggtgctcatc       420
cccaaagcca agccactcac tctgctctgg gcctacttct gcttcctcct ggccgctctg      480
ggtgtgacag ctggtgccca tcgcttgtgg agccacaggt cctaccgggc caagctgcct      540
ctgaggatat ttctggctgt cgccaactcc atggctttcc aggcagcagc agaagtggtc      600
ctgacccaga tgccctgaca gcttttcctg gtgtgatttt ggaagttaac ccttgaacag      660
aatgggtttg aactgcgcag cttcacttaa atgcatggat tttcttctgc ctccaccacc      720
tctgagacac caagatcagc ccctcctcct ctcagcctac tcaatgcaaa gaagacaagg      780
atgaagacct ttatgatgat ccacttccac ttaatgaata gtaaatatat tttctcttct      840
taaaaaaaaa aaaaaaaaaa aaaaa                                             865

<210> SEQ ID NO 9
<211> LENGTH: 2021
<212> TYPE: DNA
<213> ORGANISM: Homo sapiens

<400> SEQUENCE: 9
agccatatgg gggatacgcc agcaacagac gccggccgcc aagatctgca tccctaggcc       60
acgctaagac cctggggaag agcgcaggag cccgggagaa gggctggaag gaggggactg      120
gacgtgcgga gaattccccc ctaaaaggca gaagcccccg cccccaccct cgagctccgc      180 tcggcagag cgcctgcctg cctgccgctg ctgcgggcgc ccacctcgcc cagccatgcc      240
aggcccggcc accgacgcgg ggaagatccc ttctgcgac gccaaggaag aaatccgtgc      300
cgggctcgaa agctctgagg gcggcggcgg ccccggagagg ccaggcgcgc gcgggcagcg      360
gcagaacatc gtctggagga atgtcgtcct gatgagcttg ctccacttgg gggccgtgta      420
ctccctggtg ctcatcccca agccaagcc actcactctg ctctgggcct acttctgcct      480
cctcctggcc gctctgggtg tgacagctgg tgccatcgc ttgtggagcc acaggtccta      540
ccgggccaag ctgcctctga ggatatttct ggctgtcgcc aactccatgg ctttccagaa      600
tgacatcttc gagcggtcca gggaccaccg agccccaccac aagtactcag agacggatgc      660 tgaccccac aatgcccgcc ggggcttctt cttctcccat attgggtggc tgtttgttcg      720
caagcatcga gatgttattg agaaggggag aaagcttgac gtcactgacc tgcttgctga      780
tcctgtggtc cggatccaga gaaatacaca gcacatccag aaagaaggaa gagctctcaa      840
tcaagaggca gcgtgtgaga tgcttcgtga gtggcatcaa gggcatatat tgaaagtcac      900
ccttcccgga ttacacattt tagctttgtt acatactcat tgtaaccact ccgaaaagtg      960
ctgcttgatg ctgcgtgctc tttctgtgtc cctggaggta ttctgaaggt cagaagagag     1020
atatacaaca gcgaggcttg gtgataacgt atagaataac agacgggac tccacaccca      1080 ggccttttt aacggtgtga agcatagaca gagctgcagt ctgtgctaac attaggttat      1140
ttattgattc aatcagttga cacaaggagg cagctacggg gaggtaaaat atggtcctaa      1200
aatcaaaaag atttcagttt tgtcattctg tctctgagat tctatttcca catctagagc      1260
agggtaataa tgatacctac cttacaaaat tattgggaga atacattagt taatatatgt      1320
gaaagtatgg aggagatgtg caataaatat ttgtgttatt aactacacat acagcactct     1380
```

```
ataggagata ttccatttat aaaaacttta ggttctaaaa acctgtacac gttgattatt    1440
tttgtaagtc aaaagtgatt aagaggagtt taagctatca tttccagatg tatttctata    1500
aataaaaaca taagtatatt cagttgattt ggggtggaga gttccataga tgtctgttag    1560
gtccgcttgg tccagagctg agttcaagtc ctgaatatcc ttgttaattt tctgtcttgt    1620
tgatctgtct aatattgaca gtggggtatt aaagtctccc actattatta tatgggagtc    1680
taagtctcct tgtaggtctc taagaacttg ctttatgaat ctgggtgctc ctgtattagg    1740
tgcatacata tttaggatag ttagctcttc ttgctgcatt gatcccatta ccattatata    1800
atgcccttct ttgtcttttt tgatctttgt tggtttaaag tctgtttat tagagactag     1860 gattgcaacc cctgctattt tttttttttt ttttgcttga taaatattcc tgtatccctt    1920
tattttgagc ctatatgtgt ctttgcacgt gaggtgggtc tcctgaatac agcacaccga    1980
tgggttttga ctctaaaaaa aaaaaaaaaa aaaaaaaaa a                         2021
```

<210> SEQ ID NO 10
<211> LENGTH: 359
<212> TYPE: PRT
<213> ORGANISM: Homo sapiens

<400> SEQUENCE: 10

```
Met Pro Ala His Leu Leu Gln Asp Asp Ile Ser Ser Tyr Thr Thr
1               5                   10                  15

Thr Thr Thr Ile Thr Ala Pro Pro Gly Val Leu Gln Asn Gly Gly
                20                  25                  30

Asp Lys Leu Glu Thr Met Pro Leu Tyr Leu Glu Asp Asp Ile Arg Pro
            35                  40                  45

Asp Ile Lys Asp Asp Ile Tyr Asp Pro Thr Tyr Lys Asp Lys Glu Gly
        50                  55                  60

Pro Ser Pro Lys Val Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                85                  90                  95

Lys Phe Tyr Thr Trp Leu Trp Gly Val Phe Tyr Tyr Phe Val Ser Ala
                100                 105                 110

Leu Gly Ile Thr Ala Gly Ala His Arg Leu Trp Ser His Arg Ser Tyr
                115                 120                 125

Lys Ala Arg Leu Pro Leu Arg Leu Phe Leu Ile Ile Ala Asn Thr Met
        130                 135                 140

Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
                165                 170                 175

Phe Phe Phe Ser His Val Gly Trp Leu Leu Val Arg Lys His Pro Ala
                180                 185                 190

Val Lys Glu Lys Gly Ser Thr Leu Asp Leu Ser Asp Leu Glu Ala Glu
                195                 200                 205

Lys Leu Val Met Phe Gln Arg Arg Tyr Tyr Lys Pro Gly Leu Leu Met
        210                 215                 220

Met Cys Phe Ile Leu Pro Thr Leu Val Pro Trp Tyr Phe Trp Gly Glu
225                 230                 235                 240

Thr Phe Gln Asn Ser Val Phe Val Ala Thr Phe Leu Arg Tyr Ala Val
                245                 250                 255

Val Leu Asn Ala Thr Trp Leu Val Asn Ser Ala Ala His Leu Phe Gly
```

```
            260                 265                 270
Tyr Arg Pro Tyr Asp Lys Asn Ile Ser Pro Arg Glu Asn Ile Leu Val
            275                 280                 285

Ser Leu Gly Ala Val Gly Glu Gly Phe His Asn Tyr His His Ser Phe
            290                 295                 300

Pro Tyr Asp Tyr Ser Ala Ser Glu Tyr Arg Trp His Ile Asn Phe Asn
305                 310                 315                 320

Thr Phe Phe Ile Asp Trp Met Ala Ala Leu Gly Leu Thr Tyr Asp Arg
                325                 330                 335

Lys Lys Val Ser Lys Ala Ala Ile Leu Ala Arg Ile Lys Arg Thr Gly
                340                 345                 350

Asp Gly Asn Tyr Lys Ser Gly
            355

<210> SEQ ID NO 11
<211> LENGTH: 359
<212> TYPE: PRT
<213> ORGANISM: Homo sapiens

<400> SEQUENCE: 11

Met Pro Ala His Leu Leu Gln Asp Asp Ile Ser Ser Tyr Thr Thr Thr
1               5                   10                  15

Thr Thr Thr Ile Thr Ala Pro Pro Ser Arg Val Leu Gln Asn Gly Gly
                20                  25                  30

Asp Lys Leu Glu Thr Met Pro Leu Tyr Leu Glu Asp Asp Ile Arg Pro
            35                  40                  45

Asp Ile Lys Asp Asp Ile Tyr Asp Pro Thr Tyr Lys Asp Lys Glu Gly
        50                  55                  60

Pro Ser Pro Lys Val Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                85                  90                  95

Lys Phe Tyr Thr Trp Leu Trp Gly Val Phe Tyr Tyr Phe Val Ser Ala
                100                 105                 110

Leu Gly Ile Thr Ala Gly Ala His Arg Leu Trp Ser His Arg Ser Tyr
            115                 120                 125

Lys Ala Arg Leu Pro Leu Arg Leu Phe Leu Ile Ile Ala Asn Thr Met
        130                 135                 140

Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
                165                 170                 175

Phe Phe Phe Ser His Val Gly Trp Leu Leu Val Arg Lys His Pro Ala
            180                 185                 190

Val Lys Glu Lys Gly Ser Thr Leu Asp Leu Ser Asp Leu Glu Ala Glu
        195                 200                 205

Lys Leu Val Met Phe Gln Arg Arg Tyr Tyr Lys Pro Gly Leu Leu Leu
        210                 215                 220

Met Cys Phe Ile Leu Pro Thr Leu Val Pro Trp Tyr Phe Trp Gly Glu
225                 230                 235                 240

Thr Phe Gln Asn Ser Val Phe Val Ala Thr Phe Leu Arg Tyr Ala Val
                245                 250                 255

Val Leu Asn Ala Thr Trp Leu Val Asn Ser Ala Ala His Leu Phe Gly
            260                 265                 270
```

```
Tyr Arg Pro Tyr Asp Lys Asn Ile Ser Pro Arg Glu Asn Ile Leu Val
            275                 280                 285

Ser Leu Gly Ala Val Gly Glu Gly Phe His Asn Tyr His His Ser Phe
            290                 295                 300

Pro Tyr Asp Tyr Ser Ala Ser Glu Tyr Arg Trp His Ile Asn Phe Thr
305                 310                 315                 320

Thr Phe Phe Ile Asp Cys Met Ala Ala Leu Gly Leu Ala Tyr Asp Arg
                    325                 330                 335

Lys Lys Val Ser Lys Ala Ala Ile Leu Ala Arg Ile Lys Arg Thr Gly
                340                 345                 350

Asp Gly Asn Tyr Lys Ser Gly
            355

<210> SEQ ID NO 12
<211> LENGTH: 330
<212> TYPE: PRT
<213> ORGANISM: Homo sapiens

<400> SEQUENCE: 12

Met Pro Gly Pro Ala Thr Asp Ala Gly Lys Ile Pro Phe Cys Asp Ala
1               5                   10                  15

Lys Glu Glu Ile Arg Ala Gly Leu Glu Ser Ser Glu Gly Gly Gly Gly
                20                  25                  30

Pro Glu Arg Pro Gly Ala Arg Gly Gln Arg Gln Asn Ile Val Trp Arg
            35                  40                  45

Asn Val Val Leu Met Ser Leu Leu His Leu Gly Ala Val Tyr Ser Leu
        50                  55                  60

Val Leu Ile Pro Lys Ala Lys Pro Leu Thr Leu Leu Trp Ala Tyr Phe
65                  70                  75                  80

Cys Phe Leu Leu Ala Ala Leu Gly Val Thr Ala Gly Ala His Arg Leu
                85                  90                  95

Trp Ser His Arg Ser Tyr Arg Ala Lys Leu Pro Leu Arg Ile Phe Leu
            100                 105                 110

Ala Val Ala Asn Ser Met Ala Phe Gln Asn Asp Ile Phe Glu Trp Ser
        115                 120                 125

Arg Asp His Arg Ala His His Lys Tyr Ser Glu Thr Asp Ala Asp Pro
130                 135                 140

His Asn Ala Arg Arg Gly Phe Phe Ser His Ile Gly Trp Leu Phe Phe
145                 150                 155                 160

Val Arg Lys His Arg Asp Val Ile Glu Lys Gly Arg Lys Leu Asp Val
                165                 170                 175

Thr Asp Leu Leu Ala Asp Pro Val Val Arg Ile Gln Arg Lys Tyr Tyr
            180                 185                 190

Lys Ile Ser Val Val Leu Met Cys Phe Val Pro Thr Leu Val Pro
        195                 200                 205

Trp Tyr Ile Trp Gly Glu Ser Leu Trp Asn Ser Tyr Phe Leu Ala Ser
        210                 215                 220

Ile Leu Arg Tyr Thr Ile Ser Leu Asn Ile Ser Trp Leu Val Asn Ser
225                 230                 235                 240

Ala Ala His Met Tyr Gly Asn Arg Pro Tyr Asp Lys His Ile Ser Pro
                245                 250                 255

Arg Gln Asn Pro Leu Val Ala Leu Gly Ala Ile Gly Glu Gly Phe His
            260                 265                 270

Asn Tyr His His Thr Phe Pro Phe Asp Tyr Ser Ala Ser Glu Phe Gly
        275                 280                 285
```

```
Leu Asn Phe Asn Pro Thr Thr Trp Phe Ile Asp Phe Met Cys Trp Leu
    290                 295                 300

Gly Leu Ala Thr Asp Arg Lys Arg Ala Thr Lys Pro Met Ile Glu Ala
305                 310                 315                 320

Arg Lys Ala Arg Thr Gly Asp Ser Ser Ala
                325                 330

<210> SEQ ID NO 13
<211> LENGTH: 23
<212> TYPE: DNA
<213> ORGANISM: Homo sapiens

<400> SEQUENCE: 13
aacacatgct gatcctcata att                                              23

<210> SEQ ID NO 14
<211> LENGTH: 23
<212> TYPE: DNA
<213> ORGANISM: Homo sapiens

<400> SEQUENCE: 14
aaacagtgtg ttcgttgcca ctt                                              23

<210> SEQ ID NO 15
<211> LENGTH: 23
<212> TYPE: DNA
<213> ORGANISM: Homo sapiens

<400> SEQUENCE: 15
aaagtctcca aggccgccat ctt                                              23

<210> SEQ ID NO 16
<211> LENGTH: 23
<212> TYPE: DNA
<213> ORGANISM: Homo sapiens

<400> SEQUENCE: 16
aagaggcagc gtgtgagatg ctt                                              23

<210> SEQ ID NO 17
<211> LENGTH: 23
<212> TYPE: DNA
<213> ORGANISM: Homo sapiens

<400> SEQUENCE: 17
aaccactccg aaaagtgctg ctt                                              23

<210> SEQ ID NO 18
<211> LENGTH: 23
<212> TYPE: DNA
<213> ORGANISM: Homo sapiens

<400> SEQUENCE: 18
aacatcgtct ggaggaatgt cgt                                              23

<210> SEQ ID NO 19
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
```

```
<222> LOCATION: (1)..(19)
<223> OTHER INFORMATION: ribonucleotides

<400> SEQUENCE: 19
cacaugcuga uccucauaat t                                              21

<210> SEQ ID NO 20
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(19)
<223> OTHER INFORMATION: ribonucleotides

<400> SEQUENCE: 20
uuaugaggau cagcaugugt t                                              21

<210> SEQ ID NO 21
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(19)
<223> OTHER INFORMATION: ribonucleotides

<400> SEQUENCE: 21
acaguguguu cguugccact t                                              21

<210> SEQ ID NO 22
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(19)
<223> OTHER INFORMATION: ribonucleotides

<400> SEQUENCE: 22
guggcaacga acacacugut t                                              21

<210> SEQ ID NO 23
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(19)
<223> OTHER INFORMATION: ribonucleotides

<400> SEQUENCE: 23
agucuccaag gccgccauct t                                              21

<210> SEQ ID NO 24
<211> LENGTH: 21
<212> TYPE: DNA
<213> ORGANISM: Artificial
<220> FEATURE:
<223> OTHER INFORMATION: Synthetic Oligonucleotide
<220> FEATURE:
```

<221> NAME/KEY: misc_feature
<222> LOCATION: (1)..(19)
<223> OTHER INFORMATION: ribonucleotides

<400> SEQUENCE: 24
gauggcggcc uuggagacut t                                              21

<210> SEQ ID NO 25
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(19)
<223> OTHER INFORMATION: ribonucleotides

<400> SEQUENCE: 25
gaggcagcgu gugagaugct t                                              21

<210> SEQ ID NO 26
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(19)
<223> OTHER INFORMATION: ribonucleotides

<400> SEQUENCE: 26
gcaucucaca cgcugccuct t                                              21

<210> SEQ ID NO 27
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(19)
<223> OTHER INFORMATION: ribonucleotides

<400> SEQUENCE: 27
ccacuccgaa aagugcugct t                                              21

<210> SEQ ID NO 28
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(19)
<223> OTHER INFORMATION: ribonucleotides

<400> SEQUENCE: 28
gcagcacuuu ucggaguggt t                                              21

<210> SEQ ID NO 29
<211> LENGTH: 21
<212> TYPE: DNA
<213> ORGANISM: Artificial
<220> FEATURE:
<223> OTHER INFORMATION: Synthetic Oligonucleotide

```
<220> FEATURE:
<221> NAME/KEY: misc_feature
<222> LOCATION: (1)..(19)
<223> OTHER INFORMATION: ribonucleotides

<400> SEQUENCE: 29
caucgucugg aggaauguct t                                              21

<210> SEQ ID NO 30
<211> LENGTH: 21
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(19)
<223> OTHER INFORMATION: ribonucleotides

<400> SEQUENCE: 30
gacauuccuc cagacgaugt t                                              21
```

SCDS AS MODIFIERS OF THE P53 PATHWAY AND METHODS OF USE

REFERENCE TO RELATED APPLICATIONS

This application is a continuation of U.S. application Ser. No. 11/852,890, filed on Sep. 10, 2007, which is a continuation of U.S. application Ser. No. 10/377,133, filed on Feb. 28, 2001, which claims priority to U.S. Application Ser. No. 60/361,196, filed on Mar. 1, 2002, all of which applications are incorporated by reference herein in their entireties.

BACKGROUND OF THE INVENTION

The p53 gene is mutated in over 50 different types of human cancers, including familial and spontaneous cancers, and is believed to be the most commonly mutated gene in human cancer (Zambetti and Levine, FASEB (1993) 7:855-865; Hollstein, et al., Nucleic Acids Res, (1994) 22:3551-3555). Greater than 90% of mutations in the p53 gene are missense mutations that alter a single amino acid that inactivates p53 function. Aberrant forms of human p53 are associated with poor prognosis, more aggressive tumors, metastasis, and short survival rates (Mitsudomi at al., Clin Cancer Res 2000 October; 6 (10):4055-63; Koshland, Science (1993) 262:1953).

The human p53 protein normally functions as a central integrator of signals including DNA damage, hypoxia, nucleotide deprivation, and oncogene activation (Prives, Cell (1998) 95:5-8). In response to these signals, p53 protein levels are greatly increased with the result that the accumulated p53 activates cell cycle arrest or apoptosis depending on the nature and strength of these signals. Indeed, multiple lines of experimental evidence have pointed to a key role for p53 as a tumor suppressor (Levine, Cell (1997) 88:323-331). For example, homozygous p53 "knockout" mice are developmentally normal but exhibit nearly 100% incidence of neoplasia in the first year of life (Donehower et al., Nature (1992) 356:215-221).

The biochemical mechanisms and pathways through which p53 functions in normal and cancerous cells are not fully understood, but one clearly important aspect of p53 function is its activity as a gene-specific transcriptional activator. Among the genes with known p53-response elements are several with well-characterized roles in either regulation of the cell cycle or apoptosis, including GADD45, p21/Waf1/Cip1, cyclin G, Bax, IC3F-BP3, and MDM2 (Levine, Cell (1997) 88:323-331).

Stearoyl-CoA desaturase (SCD) is an iron-containing enzyme that catalyzes a rate-limiting step in the synthesis of unsaturated fatty acids. The principal product of SCD is oleic acid, which is formed by desaturation of stearic acid. The ratio of stearic acid to oleic acid has been implicated in the regulation of cell growth and differentiation through effects on cell-membrane fluidity and signal transduction (Zheng Y et al (1999) Nat Genet 23:268-270). SCD may play a role in obesity, and mice with a targeted disruption of the SCD had reduced body adiposity, increased insulin sensitivity, and resistance to diet-induced weight gain (Cohen P et al (2002) Science 297: 240-243; Ntambi J M et al (2002) PNAS 99: 11482-11486). Certain classes of tumors show increased expression of SCD (Chajes V et al (1999) Int J Cancer 83:585-90; Li J et al (1994) Int J Cancer 57:348-52).

The ability to manipulate the genomes of model organisms such as Drosophila provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as p53, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the p53 pathway in Drosophila, and identified their human orthologs, hereinafter referred to as Stearyl coenzyme A desaturase (SCD), The invention provides methods for utilizing these p53 modifier genes and polypeptides to identify SCD-modulating agents that are candidate therapeutic agents that can be used in the treatment of disorders associated with defective or impaired p53 function and/or SCD function. Preferred SCD-modulating agents specifically bind to SCD polypeptides and restore p53 function. Other preferred SCD-modulating agents are nucleic acid modulators such as antisense oligomers and RNAi that repress SCD gene expression or product activity by, for example, binding to and inhibiting the respective nucleic acid (i.e. DNA or mRNA).

SCD modulating agents may be evaluated by any convenient in vitro or in vivo assay for molecular interaction with an SCD polypeptide or nucleic acid. In one embodiment, candidate SCD modulating agents are tested with an assay system comprising a SCD polypeptide or nucleic acid. Agents that produce a change in the activity of the assay system relative to controls are identified as candidate p53 modulating agents. The assay system may be cell-based or cell-free. SCD-modulating agents include SCD related proteins (e.g. dominant negative mutants, and biotherapeutics); SCD-specific antibodies; SCD-specific antisense oligomers and other nucleic acid modulators; and chemical agents that specifically bind to or interact with SCD or compete with SCD binding partner (e.g. by binding to an SCD binding partner). In one specific embodiment, a small molecule modulator is identified using a desaturase assay. In specific embodiments, the screening assay system is selected from a binding assay, an apoptosis assay, a cell proliferation assay, an angiogenesis assay, and a hypoxic induction assay.

In another embodiment, candidate p53 pathway modulating agents are further tested using a second assay system that detects changes in the p53 pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the p53 pathway, such as an angiogenic, apoptotic, or cell proliferation disorder (e.g. cancer).

The invention further provides methods for modulating the SCD function and/or the p53 pathway in a mammalian cell by contacting the mammalian cell with an agent that specifically binds a SCD polypeptide or nucleic acid. The agent may be a small molecule modulator, a nucleic acid modulator, or an antibody and may be administered to a mammalian animal predetermined to have a pathology associated the p53 pathway.

DETAILED DESCRIPTION OF THE INVENTION

Genetic screens were designed to identify modifiers of the p53 pathway in *Drosophila*, where a genetic modifier screen was carried out in which p53 was overexpressed in the wing (Ollmann M, et al., Cell 2000 101: 91-101). The CG5925 gene was identified as a modifier of the p53 pathway. Accordingly, vertebrate orthologs of these modifiers, and preferably the human orthologs, SCD genes (i.e., nucleic acids and polypeptides) are attractive drug targets for the treatment of pathologies associated with a defective p53 signaling pathway, such as cancer.

In vitro and in vivo methods of assessing SCD function are provided herein. Modulation of the SCD or their respective binding partners is useful for understanding the association of the p53 pathway and its members in normal and disease conditions and for developing diagnostics and therapeutic modalities for p53 related pathologies. SCD-modulating agents that act by inhibiting or enhancing SCD expression, directly or indirectly, for example, by affecting an SCD function such as enzymatic (e.g., catalytic) or binding activity, can be identified using methods provided herein. SCD modulating agents are useful in diagnosis, therapy and pharmaceutical development.

Nucleic Acids and Polypeptides of the Invention

Sequences related to SCD nucleic acids and polypeptides that can be used in the invention are disclosed in Genbank (referenced by Genbank identifier (GI) number) as GI#s 19923295 (SEQ NO:1), 7415720 (SEQ ID NO:2), 7959734 (SEQ NO:3), 13623379 (SEQ ID NO:4), 13543283 (SEQ ID NO:5), 4808600 (SEQ NO:6), 15859548 (SEQ ID NO:7), 13436280 (SEQ ID NO:8), and 13376362 (SEQ ID NO:9) for nucleic acid, and GI#s 4826990 (SEQ NO:10), 19923296 (SEQ ID NO:11), and 15859549 (SEQ ID NO:12) for polypeptides.

The term "SCD polypeptide" refers to a full-length SCD protein or a functionally active fragment or derivative thereof. A "functionally active" SCD fragment or derivative exhibits one or more functional activities associated with a full-length, wild-type SCD protein, such as antigenic or immunogenic activity, enzymatic activity, ability to bind natural cellular substrates, etc. The functional activity of SCD proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active SCD polypeptide is a SCD derivative capable of rescuing defective endogenous SCD activity, such as in cell based or animal assays; the rescuing derivative may be from the same or a different species. For purposes herein, functionally active fragments also include those fragments that comprise one or more structural domains of an SCD, such as a binding domain. Protein domains can be identified using the PFAM program (Bateman A., et al., Nucleic Acids Res, 1999, 27:260-2). For example, the fatty acid desaturase domain (PFAM 00487) of SCD from GI#s 19923296 and 15859549 (SEQ ID NOs:11 and 12, respectively) is located respectively at approximately amino acid residues 96-321 and 71-296. Methods for obtaining SCD polypeptides are also further described below. In some embodiments, preferred fragments are functionally active, domain-containing fragments comprising at least 25 contiguous amino acids, preferably at least 50, more preferably 75, and most preferably at least 100 contiguous amino acids of any one of SEQ ID NOs:1-12 (an SCD). In further preferred embodiments, the fragment comprises the entire functionally active domain.

The term "SCD nucleic acid" refers to a DNA or RNA molecule that encodes a SCD polypeptide. Preferably, the SCD polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human SCD. Methods of identifying orthologs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *Drosophila*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of SEQ ID NOs:1-9. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of any one of SEQ ID NOs:1-9 under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of SCD Nucleic Acids and Polypeptides SCD nucleic acids and polypeptides, useful for identifying and testing agents that modulate SCD function and for other applications related to the involvement of SCD in the p53 pathway. SCD nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of an SCD protein for assays used to assess SCD function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant SCD is expressed in a cell line known to have defective p53 function (e.g. SAOS-2 osteoblasts, H1299 lung cancer cells, C33A and HT3 cervical cancer cells, HT-29 and DLD-1 colon cancer cells, among others, available from American Type Culture Collection (ATCC), Manassas, Va.). The recombinant cells are used in cell-based screening assay systems of the invention, as described further below.

The nucleotide sequence encoding an SCD polypeptide can be inserted into any appropriate expression vector. The necessary transcriptional and translational signals, including promoter/enhancer element, can derive from the native SCD gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the SCD gene product, the expression vector can comprise a promoter operably linked to an SCD gene nucleic acid, one or more origins of replication, and, one or more selectable markers (e.g. thymidine kinase activity, resistance to antibiotics, etc.). Alternatively, recombinant expression vectors can be identified by assaying for the expression of the SCD gene product based on the physical or functional properties of the SCD protein in in vitro assay systems (e.g. immunoassays).

The SCD protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the SCD gene sequence is identified, the gene product can be isolated and purified using standard methods (e.g. ion exchange, affinity, and gel exclusion chromatography; centrifugation; differential solubility; electrophoresis). Alternatively, native SCD proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of SCD or other genes associated with the p53 pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter SCD expression may be used in in vivo assays to test for activity of a candidate p53 modulating agent, or to further assess the role of SCD in a p53 pathway process such as apoptosis or cell proliferation. Preferably, the altered SCD expression results in a detectable phenotype, such as decreased or increased levels of cell proliferation, angiogenesis, or apoptosis compared to control animals having normal SCD expression. The genetically modified animal may additionally have altered p53 expression (e.g. p53 knockout). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous SCD gene that results in a decrease of SCD function, preferably such that SCD expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse SCD gene is used to construct a homologous recombination vector suitable for altering an endogenous SCD gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H at al., (1994) Scan J Immunol 40:257-264; Declerek P J et al., (1995) J Biol Chem. 270:8397-400).

In another embodiment, the transgenic animal is a "knock-in" animal having an alteration in its genome that results in altered expression (e.g., increased (including ectopic) or decreased expression) of the SCD gene, e.g., by introduction of additional copies of SCD, or by operatively inserting a regulatory sequence that provides for altered expression of an endogenous copy of the SCD gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of *Saccharomyces cerevisiae* (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the p53 pathway, as animal models of disease and disorders implicating defective p53 function, and for in vivo testing of candidate therapeutic agents, such as those identified in screens described below. The candidate therapeutic agents are administered to a genetically modified animal having altered SCD function and phenotypic changes are compared with appropriate control animals such as genetically modified animals that receive placebo treatment, and/or animals with unaltered SCD expression that receive candidate therapeutic agent.

In addition to the above-described genetically modified animals having altered SCD function, animal models having defective p53 function (and otherwise normal SCD function), can be used in the methods of the present invention. For example, a p53 knockout mouse can be used to assess, in vivo, the activity of a candidate p53 modulating agent identified in one of the in vitro assays described below. p53 knockout mice are described in the literature (Jacks et al., Nature 2001; 410:1111-1116, 1043-1044; Donehower et al., supra). Preferably, the candidate p53 modulating agent when administered to a model system with cells defective in p53 function, produces a detectable phenotypic change in the model system indicating that the p53 function is restored, i.e., the cells exhibit normal cell cycle progression.

Modulating Agents

The invention provides methods to identify agents that interact with and/or modulate the function of SCD and/or the p53 pathway. Modulating agents identified by the methods are also part of the invention. Such agents are useful in a variety of diagnostic and therapeutic applications associated with the p53 pathway, as well as in further analysis of the SCD protein and its contribution to the p53 pathway. Accordingly, the invention also provides methods for modulating the p53 pathway comprising the step of specifically modulating SCD activity by administering a SCD-interacting or -modulating agent.

As used herein, an "SCD-modulating agent" is any agent that modulates SCD function, for example, an agent that interacts with SCD to inhibit or enhance SCD activity or otherwise affect normal SCD function. SCD function can be affected at any level, including transcription, protein expression, protein localization, and cellular or extra-cellular activity. In a preferred embodiment, the SCD-modulating agent specifically modulates the function of the SCD. The phrases "specific modulating agent", "specifically modulates", etc., are used herein to refer to modulating agents that directly bind to the SCD polypeptide or nucleic acid, and preferably inhibit, enhance, or otherwise alter, the function of the SCD. These phrases also encompass modulating agents that alter the interaction of the SCD with a binding partner, substrate, or cofactor (e.g. by binding to a binding partner of an SCD, or to a protein/binding partner complex, and altering SCD function). In a further preferred embodiment, the SCD-modulating agent is a modulator of the p53 pathway (e.g. it restores and/or upregulates p53 function) and thus is also a p53-modulating agent.

Preferred SCD-modulating agents include small molecule compounds; SCD-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Synthetic compounds may be rationally designed or identified based on known or inferred properties of the SCD protein or may be identified by screening compound libraries. Alternative appropriate modulators of this class are natural products, particularly secondary metabolites from organisms such as plants or fungi, which can also be identified by screening compound libraries for SCD-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the p53 pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific SCD-interacting proteins are useful in a variety of diagnostic and therapeutic applications related to the p53 pathway and related disorders, as well as in validation assays for other SCD-modulating agents. In a preferred embodiment, SCD-interacting proteins affect normal SCD function, including transcription, protein expression, protein localization, and cellular or extra-cellular activity. In another embodiment, SCD-interacting proteins are useful in detecting and providing information about the function of SCD proteins, as is relevant to p53 related disorders, such as cancer (e.g., for diagnostic means).

An SCD-interacting protein may be endogenous, i.e. one that naturally interacts genetically or biochemically with an SCD, such as a member of the SCD pathway that modulates SCD expression, localization, and/or activity. SCD-modulators include dominant negative forms of SCD-interacting proteins and of SCD proteins themselves. Yeast two-hybrid and variant screens offer preferred methods for identifying endogenous SCD-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R $3^{rd}$, Trends Genet (2000) 16:5-8).

An SCD-interacting protein may be an exogenous protein, such as an SCD-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). SCD antibodies are further discussed below.

In preferred embodiments, an SCD-interacting protein specifically binds an SCD protein. In alternative preferred embodiments, an SCD-modulating agent binds an SCD substrate, binding partner, or cofactor.

Antibodies

In another embodiment, the protein modulator is an SCD specific antibody agonist or antagonist. The antibodies have therapeutic and diagnostic utilities, and can be used in screening assays to identify SCD modulators. The antibodies can also be used in dissecting the portions of the SCD pathway responsible for various cellular responses and in the general processing and maturation of the SCD.

Antibodies that specifically bind SCD polypeptides can be generated using known methods. Preferably the antibody is specific to a mammalian ortholog of SCD polypeptide, and more preferably, to human SCD. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of SCD which are particularly antigenic can be selected, for example, by routine screening of SCD polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence shown in SEQ ID NOs:10-12. Monoclonal antibodies with affinities of $10^8 M^{-1}$ preferably $10^9$ $M^{-1}$ to $10^{10}$ $M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of SCD or substantially purified fragments thereof. If SCD fragments are used, they preferably comprise at least 10, and more preferably, at least 20 contiguous amino acids of an SCD protein. In a particular embodiment, SCD-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of SCD-specific antibodies is assayed by an appropriate assay such as a solid phase enzyme-linked immunosorbant assay (ELISA) using immobilized corresponding SCD polypeptides. Other assays, such as radioimmunoassays or fluorescent assays might also be used.

Chimeric antibodies specific to SCD polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

SCD-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334; 544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg—to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859, 206; WO0073469).

Specific Biotherapeutics

In a preferred embodiment, an SCD-interacting protein may have biotherapeutic applications. Biotherapeutic agents formulated in pharmaceutically acceptable carriers and dosages may be used to activate or inhibit signal transduction pathways. This modulation may be accomplished by binding a ligand, thus inhibiting the activity of the pathway; or by binding a receptor, either to inhibit activation of, or to activate, the receptor. Alternatively, the biotherapeutic may itself be a ligand capable of activating or inhibiting a receptor. Biotherapeutic agents and methods of producing them are described in detail in U.S. Pat. No. 6,146,628.

When the SCD is a ligand, it may be used as a biotherapeutic agent to activate or inhibit its natural receptor. Alternatively, antibodies against SCD, as described in the previous section, may be used as biotherapeutic agents.

When the SCD is a receptor, its ligand(s), antibodies to the ligand(s) or the SCD itself may be used as biotherapeutics to modulate the activity of SCD in the p53 pathway.

Nucleic Acid Modulators

Other preferred SCD-modulating agents comprise nucleic acid molecules, such as antisense oligomers or double stranded RNA (dsRNA), which generally inhibit SCD activity. Preferred nucleic acid modulators interfere with the function of the SCD nucleic acid such as DNA replication, transcription, translocation of the SCD RNA to the site of protein translation, translation of protein from the SCD RNA, splicing of the SCD RNA to yield one or more mRNA species, or catalytic activity which may be engaged in or facilitated by the SCD RNA.

In one embodiment, the antisense oligomer is an oligonucleotide that is sufficiently complementary to an SCD mRNA to bind to and prevent translation, preferably by binding to the 5' untranslated region. SCD-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22 (3):271-281; Summerton J, and Weller D. 1997 Antisense Nucleic Acid Drug Dev. :7:187-95; U.S. Pat. No. 5,235,033; and U.S. Pat. No. 5,378,841).

Alternative preferred SCD nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in *C. elegans, Drosophila*, plants, and humans are known in the art (Fire A, at al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet, 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., at al., Cell 101, 25-33 (2000); Bernstein, E., at al., Nature 409, 363-366 (2001); Elbashir, S. M., at al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, an SCD-specific nucleic acid modulator is used in an assay to further elucidate the role of the SCD in the p53 pathway, and/or its relationship to other members of the pathway. In another aspect of the invention, an SCD-specific antisense oligomer is used as a therapeutic agent for treatment of p53-related disease states.

Assay Systems

The invention provides assay systems and screening methods for identifying specific modulators of SCD activity. As used herein, an "assay system" encompasses all the components required for performing and analyzing results of an assay that detects and/or measures a particular event. In general, primary assays are used to identify or confirm a modulator's specific biochemical or molecular effect with respect to the SCD nucleic acid or protein. In general, secondary assays further assess the activity of a SCD modulating agent identified by a primary assay and may confirm that the modulating agent affects SCD in a manner relevant to the p53 pathway. In some cases, SCD modulators will be directly tested in a secondary assay.

In a preferred embodiment, the screening method comprises contacting a suitable assay system comprising an SCD polypeptide or nucleic acid with a candidate agent under conditions whereby, but for the presence of the agent, the system provides a reference activity (e.g. desaturase activity), which is based on the particular molecular event the screening method detects. A statistically significant difference between the agent-biased activity and the reference activity indicates that the candidate agent modulates SCD activity, and hence the p53 pathway. The SCD polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of SCD and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when SCD-interacting proteins are used in screens to identify small molecule modulators, the binding specificity of the interacting protein to the SCD protein may be assayed by various known methods such as substrate processing (e.g. ability of the candidate SCD-specific binding agents to function as negative effectors in SCD-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit SCD specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a SCD polypeptide, a fusion protein thereof, or to cells or membranes bearing the polypeptide or fusion protein. The SCD polypeptide can be full length or a fragment thereof that retains functional SCD activity. The SCD polypeptide may be fused to another polypeptide, such as a peptide tag for detection or anchoring, or to another tag. The SCD polypeptide is preferably human SCD, or is an ortholog or derivative thereof as described above. In a preferred embodiment, the screening assay detects candidate agent-based modulation of SCD interaction with a binding target, such as an endogenous or exogenous protein or other substrate that has SCD-specific binding activity, and can be used to assess normal SCD gene function.

Suitable assay formats that may be adapted to screen for SCD modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate SCD and p53 pathway modulators (e.g. U.S. Pat. Nos. 5,550,019 and 6,133,437 (apoptosis assays); U.S. Pat. No. 6,020,135 (p53 modulation), and U.S. Pat. Nos. 5,976, 782, 6,225,118 and 6,444,434 (angiogenesis assays), among others). Specific preferred assays are described in more detail below.

Fatty acid desaturases catalyze the insertion of double bonds into saturated fatty acid molecules. In one application, radioassays for inhibitors of delta-5 and delta-6 fatty acid desaturase activity use thin layer chromatography to detect conversion of fatty acid substrates (Obukowicz et al., Biochem Pharmacol (1998) 55:1045-1058).

Apoptosis Assays

Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). An apoptosis assay system may comprise a cell that expresses an SCD, and that optionally has defective p53 function (e.g. p53 is over-expressed or under-expressed relative to wild-type cells). A test agent can be added to the apoptosis assay system and changes in induction of apoptosis relative to controls where no test agent is added, identify candidate p53 modulating agents. In some embodiments of the invention, an apoptosis assay may be used as a secondary assay to test a candidate p53 modulating agents that is initially identified using a cell-free assay system. An apoptosis assay may also be used to test whether SCD function plays a direct role in apoptosis. For example, an apoptosis assay may be performed on cells that over- or under-express SCD relative to wild type cells. Differences in apoptotic response compared to wild type cells suggests that the SCD plays a direct role in the apoptotic response. Apoptosis assays are described further in U.S. Pat. No. 6,133,437.

Cell Proliferation and Cell Cycle Assays

Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H-3. (Chadlee, D. N. 1995, J. Biol. Chem 270:20098-105). Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46).

Cell proliferation may also be assayed by colony formation in soft agar (Sambrook et al., Molecular Cloning, Cold Spring Harbor (1989)). For example, cells transformed with SCD are seeded in soft agar plates, and colonies are measured and counted after two weeks incubation.

Involvement of a gene in the cell cycle may be assayed by flow cytometry (Gray J W at al. (1986) Int J Radiat Biol Relat Stud Phys Chem Med 49:237-55). Cells transfected with an SCD may be stained with propidium iodide and evaluated in a flow cytometer (available from Becton Dickinson), which indicates accumulation of cells in different stages of the cell cycle.

Accordingly, a cell proliferation or cell cycle assay system may comprise a cell that expresses an SCD, and that optionally has defective p53 function (e.g. p53 is over-expressed or under-expressed relative to wild-type cells). A test agent can be added to the assay system and changes in cell proliferation or cell cycle relative to controls where no test agent is added, identify candidate p53 modulating agents. In some embodiments of the invention, the cell proliferation or cell cycle assay may be used as a secondary assay to test a candidate p53 modulating agents that is initially identified using another assay system such as a cell-free assay system. A cell proliferation assay may also be used to test whether SCD function plays a direct role in cell proliferation or cell cycle. For example, a cell proliferation or cell cycle assay may be performed on cells that over- or under-express SCD relative to wild type cells. Differences in proliferation or cell cycle compared to wild type cells suggests that the SCD plays a direct role in cell proliferation or cell cycle.

Angiogenesis

Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses an SCD, and that optionally has defective p53 function (e.g. p53 is over-expressed or under-expressed relative to wild-type cells). A test agent can be added to the angiogenesis assay system and changes in angiogenesis relative to controls where no test agent is added, identify candidate p53 modulating agents. In some embodiments of the invention, the angiogenesis assay may be used as a secondary assay to test a candidate p53 modulating agents that is initially identified using another assay system. An angiogenesis assay may also be used to test whether SCD function plays a direct role in cell proliferation. For example, an angiogenesis assay may be performed on cells that over- or under-express SCD relative to wild type cells. Differences in angiogenesis compared to wild type cells suggests that the SCD plays a direct role in angiogenesis. U.S. Pat. Nos. 5,976,782, 6,225,118 and 6,444,434, among others, describe various angiogenesis assays.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with SCD in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses an SCD, and that optionally has defective p53 function (e.g. p53 is over-expressed or under-expressed relative to wild-type cells). A test agent can be added to the hypoxic induction assay system and changes in hypoxic response relative to controls where no test agent is added, identify candidate p53 modulating agents. In some embodiments of the invention, the hypoxic induction assay may be used as a secondary assay to test a candidate p53 modulating agents that is initially identified using another assay system. A hypoxic induction assay may also be used to test whether SCD function plays a direct role in the hypoxic response. For example, a hypoxic induction assay may be performed on cells that over- or under-express SCD relative to wild type cells. Differences in hypoxic response compared to wild type cells suggests that the SCD plays a direct role in hypoxic induction.

Cell Adhesion

Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12 (3):346-53).

Tubulogenesis

Tubulogenesis assays monitor the ability of cultured cells, generally endothelial cells, to form tubular structures on a matrix substrate, which generally simulates the environment of the extracellular matrix. Exemplary substrates include Matrigel™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. Serum represents an undefined source of growth factors. In a preferred embodiment, the assay is performed with cells cultured in serum free medium, in order to control which process or pathway a candidate agent modulates. Moreover, we have found that different target genes respond differently to stimulation with different pro-angiogenic agents, including inflammatory angiogenic factors such as TNF-alpa. Thus, in a further preferred embodiment, a tubulogenesis assay system comprises testing an SCD's response to a variety of factors, such as FGF, VEGF, phorbol myristate acetate (PMA), TNF-alpha, ephrin, etc.

Cell Migration

An invasion/migration assay (also called a migration assay) tests the ability of cells to overcome a physical barrier and to migrate towards pro-angiogenic signals. Migration assays are known in the art (e.g., Paik J H et al., 2001, J Biol Chem 276:11830-11837). In a typical experimental set-up, cultured endothelial cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific, South San Francisco, Calif.), or by any other method for determining cell number. In another exemplary set up, cells are fluorescently labeled and migration is detected using fluorescent readings, for instance using the Falcon HITS FluoroBlok (Becton Dickinson). While some migration is observed in the absence of stimulus, migration is greatly increased in response to pro-angiogenic factors. As described above, a preferred assay system for migration/invasion assays comprises testing an SCD's response to a variety of pro-angiogenic factors, including tumor angiogenic and inflammatory angiogenic agents, and culturing the cells in serum free medium.

Sprouting Assay

A sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143: 1341-52, 1998). Spheroids are harvested and seeded in 900 µl of methocel-collagen solution and pipetted into individual wells of a 24 well plate to allow collagen gel polymerization. Test agents are added after 30 min by pipetting 100 µl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

Primary Assays for Antibody Modulators

For antibody modulators, appropriate primary assays test is a binding assay that tests the antibody's affinity to and specificity for the SCD protein. Methods for testing antibody affinity and specificity are well known in the art (Harlow and Lane, 1988, 1999, supra). The enzyme-linked immunosorbant assay (ELISA) is a preferred method for detecting SCD-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance SCD gene expression, preferably mRNA expression. In general, expression analysis comprises comparing SCD expression in like populations of cells (e.g., two pools of cells that endogenously or recombinantly express SCD) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that SCD mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the SCD protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve SCD mRNA expression, may also be used to test nucleic acid modulators.

Secondary Assays

Secondary assays may be used to further assess the activity of SCD-modulating agent identified by any of the above methods to confirm that the modulating agent affects SCD in a manner relevant to the p53 pathway. As used herein, SCD-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with SCD.

Secondary assays generally compare like populations of cells or animals (e.g., two pools of cells or animals that endogenously or recombinantly express SCD) in the presence and absence of the candidate modulator. In general, such assays test whether treatment of cells or animals with a candidate SCD-modulating agent results in changes in the p53 pathway in comparison to untreated (or mock- or placebo-treated) cells or animals. Certain assays use "sensitized genetic backgrounds", which, as used herein, describe cells or animals engineered for altered expression of genes in the p53 or interacting pathways.

Cell-Based Assays

Cell based assays may use a variety of mammalian cell lines known to have defective p53 function (e.g. SAOS-2 osteoblasts, H1299 lung cancer cells, C33A and HT3 cervical cancer cells, HT-29 and DLD-1 colon cancer cells, among others, available from American Type Culture Collection (ATCC), Manassas, Va.). Cell based assays may detect endogenous p53 pathway activity or may rely on recombinant expression of p53 pathway components. Any of the aforementioned assays may be used in this cell-based format. Candidate modulators are typically added to the cell media but may also be injected into cells or delivered by any other efficacious means.

Animal Assays

A variety of non-human animal models of normal or defective p53 pathway may be used to test candidate SCD modulators. Models for defective p53 pathway typically use genetically modified animals that have been engineered to mis-express (e.g., over-express or lack expression in) genes involved in the p53 pathway. Assays generally require systemic delivery of the candidate modulators, such as by oral administration, injection, etc.

In a preferred embodiment, p53 pathway activity is assessed by monitoring neovascularization and angiogenesis. Animal models with defective and normal p53 are used to test the candidate modulator's affect on SCD in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the SCD. The mixture is then injected subcutaneously (SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on SCD is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the SCD endogenously are injected in the flank, $1\times10^5$ to $1\times10^7$ cells per mouse in a volume of 100 μL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors may be utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MIT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic And Therapeutic Uses

Specific SCD-modulating agents are useful in a variety of diagnostic and therapeutic applications where disease or disease prognosis is related to defects in the p53 pathway, such as angiogenic, apoptotic, or cell proliferation disorders. Accordingly, the invention also provides methods for modulating the p53 pathway in a cell, preferably a cell pre-determined to have defective or impaired p53 function (e.g. due to overexpression, underexpression, or misexpression of p53, or due to gene mutations), comprising the step of administering an agent to the cell that specifically modulates SCD activity. Preferably, the modulating agent produces a detectable phenotypic change in the cell indicating that the p53 function is restored. The phrase "function is restored", and equivalents, as used herein, means that the desired phenotype is achieved, or is brought closer to normal compared to untreated cells. For example, with restored p53 function, cell proliferation and/or progression through cell cycle may normalize, or be brought closer to normal relative to untreated cells. The invention also provides methods for treating disorders or disease associated with impaired p53 function by administering a therapeutically effective amount of an SCD-modulating agent that modulates the p53 pathway. The invention further provides methods for modulating SCD function in a cell, preferably a cell pre-determined to have defective or impaired SCD function, by administering an SCD-modulating agent. Additionally, the invention provides a method for treating disorders or disease associated with impaired SCD function by administering a therapeutically effective amount of an SCD-modulating agent.

The discovery that SCD is implicated in p53 pathway provides for a variety of methods that can be employed for the diagnostic and prognostic evaluation of diseases and disorders involving defects in the p53 pathway and for the identification of subjects having a predisposition to such diseases and disorders.

Various expression analysis methods can be used to diagnose whether SCD expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective p53 signaling that express an SCD, are identified as amenable to treatment with an SCD modulating agent. In a preferred application, the p53 defective tissue overexpresses an SCD relative to normal tissue. For example, a Northern blot analysis of mRNA from tumor and normal cell lines, or from tumor and matching normal tissue samples from the same patient, using full or partial SCD cDNA sequences as probes, can determine whether particular tumors express or overexpress SCD. Alternatively, the TaqMan® is used for quantitative RT-PCR analysis of SCD expression in cell lines, normal tissues and tumor samples (PE Applied Biosystems).

Various other diagnostic methods may be performed, for example, utilizing reagents such as the SCD oligonucleotides, and antibodies directed against an SCD, as described above for: (1) the detection of the presence of SCD gene mutations, or the detection of either over- or under-expression of SCD mRNA relative to the non-disorder state; (2) the detection of either an over- or an under-abundance of SCD gene product relative to the non-disorder state; and (3) the detection of perturbations or abnormalities in the signal transduction pathway mediated by SCD.

Thus, in a specific embodiment, the invention is drawn to a method for diagnosing a disease or disorder in a patient that is associated with alterations in SCD expression, the method comprising: a) obtaining a biological sample from the patient; b) contacting the sample with a probe for SCD expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *Drosophila* p53 Screen

The *Drosophila* p53 gene was overexpressed specifically in the wing using the vestigial margin quadrant enhancer. Increasing quantities of *Drosophila* p53 (titrated using different strength transgenic inserts in 1 or 2 copies) caused deterioration of normal wing morphology from mild to strong, with phenotypes including disruption of pattern and polarity of wing hairs, shortening and thickening of wing veins, progressive crumpling of the wing and appearance of dark "death" inclusions in wing blade. In a screen designed to identify enhancers and suppressors of *Drosophila* p53, homozygous females carrying two copies of p53 were crossed to 5663 males carrying random insertions of a piggyBac transposon (Fraser M et al., Virology (1985) 145:356-361). Progeny containing insertions were compared to noninsertion-bearing sibling progeny for enhancement or suppression of the p53 phenotypes. Sequence information surrounding the piggyBac insertion site was used to identify the modifier genes. Modifiers of the wing phenotype were identified as members of the p53 pathway. CG5925 was an enhancer of the wing phenotype. Orthologs of the modifiers are referred to herein as SCD.

BLAST analysis (Altschul et al., supra) was employed to identify orthologs of *Drosophila* modifiers. For example, representative sequences from SCD, GI#s 19923296 and 15859549 (SEQ ID NOs:11 and 12, respectively), share 59% and 53% amino acid identity, respectively, with the *Drosophila* CG5925.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27 (1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the *Caenorhabditis elegans* genome and identification of human orthologs. Genome Res. 2000 November; 10 (11):1679-89) programs. For example, the fatty acid desaturase domain (PFAM 00487) of SCD from GI#s 19923296 and 15859549 (SEQ NOs:11 and 12, respectively) is located respectively at approximately amino acid residues 96-321 and 71-296. Further, SCDs appear to have transmembrane domains. The transmembrane domains of SEQ ID NO:11 have start and end coordinates which are located at approximately amino acid residues (71, 93) (98, 120) (221, 238) (251, 273), and transmembrane domains of SEQ NO:12 have start and end coordinates which are located at approximately amino acid residues (45, 67) (72, 94) (194, 212) (216, 238).

D. High-Throughput In Vitro Fluorescence Polarization Assay

Fluorescently-labeled SCD peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microliter System (Dynatech Laboratories, Inc), relative to control values indicates the test compound is a candidate modifier of SCD activity.

III. High-Throughput In Vitro Binding Assay $^{33}$P-labeled SCD peptide is added in an assay buffer (100 mM KCl, 20 mM HEPES pH 7.6, 1 mM MgCl$_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate p53 modulating agents.

IV. Immunoprecipitations and Immunoblotting

For coprecipitation of transfected proteins, 3×10$^6$ appropriate recombinant cells containing the SCD proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P.40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, UC Davis, Clontech, Stratagene, Ardais, Genome Collaborative, and Ambion.

TaqMan analysis was used to assess expression levels of the disclosed genes in various samples.

RNA was extracted from each tissue sample using Qiagen (Valencia, Calif.) RNeasy kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of Applied Biosystems (Foster City, Calif.).

Primers for expression analysis using TaqMan assay (Applied Biosystems, Foster City, Calif.) were prepared according to the TaqMan protocols, and the following criteria: a) primer pairs were designed to span introns to eliminate genomic contamination, and b) each primer pair produced only one product. Expression analysis was performed using a 7900HT instrument.

Taqman reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average (all normal samples)>2× STDEV (all normal samples)).

Results are shown in Table 1. Number of pairs of tumor samples and matched normal tissue from the same patient are shown for each tumor type. Percentage of the samples with at least two-fold overexpression for each tumor type is provided. ND stands for not done. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

taining 19 ribonucleotides followed by 2 deoxy-ribonucleotides (dTdT), and shown in the SEQ IDs as YY, at the 3' terminus. The sequences for each oligonucleotide are:

```
SCD 1-sense (SEQ ID NO: 19):
CACAUGCUGAUCCUCAUAAYY;

SCD1-antisense (SEQ ID NO: 20):
UUAUGAGGAUCAGCAUGUGYY;

SCD2-sense (SEQ ID NO: 21):
ACAGUGUGUUCGUUGCCACYY;

SCD2-antisense (SEQ ID NO: 22):
GUGGCAACGAACACACUGUYY;

SCD3-sense (SEQ ID NO: 23):
AGUCUCCAAGGCCGCCAUCYY;

SCD3-antisense (SEQ ID NO: 24):
GAUGGCGGCCUUGGAGACUYY;

Deasat1-sense (SEQ ID NO: 25):
GAGGCAGCGUGUGAGAUGCYY;

Deasat1-antisense (SEQ ID NO: 26):
GCAUCUCACACGCUGCCUCYY;

Deasat2-sense (SEQ ID NO: 27):
CCACUCCGAAAAGUGCUGCYY;
```

TABLE 1

| GI# | SEQ ID NO: | Breast | # of Pairs | Colon | # of Pairs | Head and Neck | # of Pairs | Kidney | # of Pairs | Lung | # of Pairs | Ovary | # of Pairs | Prostate | # of Pairs | Skin | # of Pairs | Uterus | # of Pairs |
|---|---|---|---|---|---|---|---|---|---|---|---|---|---|---|---|---|---|---|---|
| 19923295 | 1 | 33% | 21 | 67% | 33 | 25% | 8 | 83% | 24 | 10% | 21 | 36% | 11 | 17% | 12 | 33% | 3 | 58% | 19 |
| 13436280; 13376362 | 8; 9 | 44% | 36 | 27% | 37 | ND | ND | ND | ND | 35% | 37 | 39% | 18 | 35% | 20 | ND | ND | 62% | 21 |
| 13376362 | 9 | 48% | 21 | 42% | 33' | 88% | 8 | 22% | 23 | 38% | 21 | 45% | 11 | 8% | 12 | 33% | 3 | 37% | 19 |
| 13436280 | 8 | 42% | 19 | 39% | 33 | 38% | 8 | 8% | 24 | 25% | 20 | 56% | 9 | 25% | 12 | 67% | 3 | 50% | 18 |

VI. Inhibition of SCD by RNA Interference

To understand the role of the SCD enzymes in the survival and proliferation of tumor cells, small interfering RNAs (siRNAs) were designed to cause the specific destruction of the mRNAs corresponding to SEQ ID NO:1 and SEQ ID NO:9. The sequences from SEQ ID NO:1 selected for siRNA generation are

```
SCD1 (SEQ ID NO: 13):
AACACATGCTGATCCTCATAATT;
SCD2 (SEQ ID NO: 14):
AAACAGTGTGTTCGTTGCCACTT;
SCD3 (SEQ ID NO: 15):
AAAGTCTCCAAGGCCGCCATCTT.
```

The sequences from SEQ ID NO:9 selected for siRNA generation are

```
Desat1 (SEQ ID NO: 16):
AAGAGGCAGCGTGTGAGATGCTT;
Desat2 (SEQ ID NO: 17):
AACCACTCCGAAAAGTGCTGCTT;
Desat3 (SEQ ID NO: 18):
AACATCGTCTGGAGGAATGTCGT.
```

For each siRNA, two 21-mer oligonucleotides were custom synthesized by Qiagen (Valencia, Calif.) including a sense oligonucleotide and an antisense oligonucleotide each con- -continued

```
Deasat2-antisense (SEQ ID NO: 28):
GCAGCACUUUUCGGAGUGGYY;

Deasat3-sense (SEQ ID NO: 29):
CAUCGUCUGGAGGAAUGUCYY;

Deasat3-antisense (SEQ ID NO: 30):
GACAUUCCUCCAGACGAUGYY.
```

Small interfering RNAs were prepared by combining corresponding sense and antisense oligonucleotides at 20 µM each in a buffer solution containing 100 mM potassium acetate, 2 mM magnesium acetate and 30 mM Hepes-KOH buffer, pH 7.4. Efficient annealing of duplex oligonucleotides was achieved by incubation of the combined oligos at 90 degrees C. for 1 minute followed by further incubation at 37 degrees C. for 1 hour. To cause specific mRNA degradation and subsequent reduction of cellular SCD proteins, siRNA duplexes were transfected into human cancer cells at a final concentration of 100 nM using Lipofectamine 2000 (Invitrogen, Carlsbad, Calif.) at 1 µg/ml according to the manufacturers protocol. Forty-eight hours following transfection, the levels of SCD proteins (SEQ ID NO:10, 11 and 12) were determined by immunoblotting using specific antibodies.

Small Inhibitory RNA (siRNA) Effects on Cell Cycle Parameters

The effects of siRNAs directed against the sequence of SEQ ID NO:1 or SEQ ID NO:9 on the cycle progression of five human tumor cell lines were examined. The cells lines under examination were derived from lung (A549, LX1), prostate (LnCAP), breast (SKBR3), and colon (HCT116) tumors. Briefly, 100 nM of each siRNA duplex was transfected in the indicated cell lines using Lipofectamine 2000 (Invitrogen, Carlsbad, Calif.) at a final concentration of 1 µml. Approximately seventy-two hours post transfection the cells were trypsinized, fixed in ethanol and incubated with propidium iodide (PI) as a marker of DNA content. The PI stained cells were then subjected to fluorescent activated cell sorting (FACS) to visualize the G1, S, G2/M and sub-G1 stages of the cell cycle. After treatment of cells with siRNAs directed against SEQ ID NO:9 and analysis by FACS, no pronounced effects on the cell cycle parameters were observed for the tumor cell lines under examination suggesting that down regulation of SEQ ID NO:9 mRNA does not affect tumor cell line cell cycle progression. In contrast, siRNAs directed against SEQ ID NO:1 resulted in a more pronounced effect on the cell cycle parameters of several of the tumor cell lines compared to cells treated with a negative control (Ctrl-XR) siRNA duplex. The siRNA directed against SEQ ID NO:1 induced a sub-G1 population of PI-stained SKBR3, LX1, and A549 cells consistent with the induction of apoptosis in these cell lines. These results indicate that down regulation of SEQ ID NO:1 alters the cell cycle progression of multiple tumor cell lines and that chemical modulation of SEQ ID NO:1 may be useful for the treatment of these tumors.

Small Inhibitory RNA (siRNA) Effects on Cell Growth and Survival

The effects of siRNAs directed against the sequence of SEQ ID NO: 1 or SEQ ID NO: 9 on the growth and survival of five human tumor cell lines were examined. The cells lines examined included LX1, A549, LnCAP, SKBR3 and HCT116. Briefly, 100 nM of each siRNA duplex was transfected in the indicated cell lines using Lipofectamine 2000 (Invitrogen, Carlsbad, Calif.) at a final concentration of 1 µg/ml. Approximately seventy-two hours after transfection of cells in 96 well plates, cultures were analyzed for the total number of viable cells using the Cell Titer 96 MTS assay kit (Promega, Madison, Wis.) according to the manufacturer's instructions. After treatment with siRNAs against SEQ ID NO:1 significant growth inhibition was observed relative to cells treated with negative control siRNAs (Ctrl-XR and SKIP3). The level of growth inhibition observed after targeting SEQ ID NO:1 was comparable to that seen in cells treated with siRNAs targeting CyclinD1 (cycD) a known cancer gene and a positive control for siRNA-mediated growth inhibition. Similar growth inhibitory effects were demonstrated when LNCAP and SKBR3 cells were treated with siRNAs targeting SEQ ID NO:9. These results demonstrate that suppression of SEQ ID NO:1 and SEQ ID NO:9 mRNAs inhibits the overall cell growth in cancer cell lines suggesting that modulation of these molecules may have utility in the treatment of proliferative diseases including cancer.

Small Inhibitory RNA (siRNA) Effects on Apoptosis

The ability of siRNAs directed against the sequence of SEQ ID NO: 1 or SEQ ID NO: 9 to induce apoptosis (programmed cell death) in human cancer cell lines was tested. The cells lines examined were A549 and LX1, both lung cancer cells lines. Briefly, 100 nM of each siRNA duplex was transfected in the indicated cell lines using Lipofectamine 2000 (Invitrogen, Carlsbad, Calif.) at a final concentration of 1 µg/ml. Approximately seventy-two hours after transfection of cells in 96 well plates, cultures were analyzed for the induction of apoptotic cell death using the Cell Death Detection ELISA kit (Roche Molecular Biochemicals, Indianapolis, Ind.) according to the manufacturer's instructions. This assay measures the amount of cytoplasmic, histone-associated DNA fragments in the culture, an indicator of the number of apoptotic cells present. After treatment with siRNAs against SEQ ID NO:1 significant induction of apoptosis was observed relative to cells treated with negative control siRNAs (Ctrl-XR and SKIP4). The level of growth inhibition observed after targeting SEQ ID NO:1 was even higher than that seen in cells treated with siRNAs targeting CyclinD1 (cycD), a positive control in this assay. However, in cells treated with siRNAs targeting SEQ ID NO:9 no increase in apoptosis relative to controls was observed. These results are consistent with the findings from the cell cycle parameter analysis and demonstrate that suppression of SEQ NO:1 can initiate apoptosis, an important mechanism of cell death in cancer cells. These results further suggest that modulation of SCDs may have utility in the treatment of cancer.

VII. NIH/3T3 Foci Formation Assay

To determine if SEQ ID NO:9 or SEQ ID NO:1 could promote malignant transformation, these sequences were examined for the ability to promote foci formation in NIH/3T3 cells, an indicator of loss of contact inhibition and predictor of oncogenic potential. These sequences were transferred into a mammalian expression vector, pcDNA4.0TOmyc, and 10 µg of each plasmid was transfected into $1 \times 10^5$ NIH/3T3 cells plated on a 10 cm$^2$ dish using Lipofectamine Plus reagent. Cells were grown in DMEM containing 5% calf serum until foci formation was observed (14-21 days). Transfection efficiency and the establishment of stable clonal populations was performed in parallel transfections where the cells were grown in DMEM/5% calf serum containing 750 µg/ml of 0418 or the appropriate antibiotic for selection. After 21 days in culture SEQ ID NO:1 and SEQ NO:9 transfections cultured without antibiotics were fixed in 4% Formalin (Sigma), washed with PBS and stained with Geimsa in PBS for 4 hours at 37° C. Geimsa-stained foci where counted visually. Neither SEQ ID NO:9 or SEQ NO:1 resulted in foci formation alone or in combination with subthreshold amounts of known transforming sequences (Ras, c-myc, or Rho).

The invention claimed is:

1. A method of identifying a candidate p53 pathway enhancing agent, said method comprising the steps of:
   (a) providing a first assay system comprising cultured cells that express a stearoyl-CoA desaturase (SCD) nucleic acid encoding the SCD polypeptide of SEQ ID NO: 11;
   (b) contacting the first assay system with a candidate test agent;
   (c) measuring the expression of said SCD nucleic acid in the first assay system in the presence and absence of said candidate test agent;
   (d) identifying the test agent as a candidate p53 pathway enhancing agent by detecting a decrease in the expression of SCD nucleic acid in the presence of said test agent;
   (e) providing a second assay system comprising cultured cells expressing said SCD polypeptide, wherein the second assay system is capable of detecting an enhancement in the p53 pathway and wherein the assay of the second assay system is selected from the group consisting of an apoptosis assay, a cell proliferation assay, an angiogenesis assay, and a hypoxic induction assay;
   (f) contacting the second assay system with the test agent of (b); and
   (g) confirming the test agent as a p53 pathway enhancing agent by detecting an enhancement in the second assay system.

2. The method of claim 1, wherein the cultured cells of the first assay system additionally have defective p53 function.

3. The method of claim 1, wherein the candidate test agent is a nucleic acid modulator against said SCD nucleic acid.

4. The method of claim 3, wherein the nucleic acid modulator is an antisense oligomer.

5. The method of claim 4, wherein the nucleic acid modulator is a PMO.

6. The method of claim 3, wherein the nucleic acid modulator is an siRNA.

* * * * *